United States Patent
Jenson et al.

(10) Patent No.: US 8,758,402 B2
(45) Date of Patent: Jun. 24, 2014

(54) TISSUE PUNCTURE CLOSURE DEVICE

(75) Inventors: Mark L. Jenson, Greenfield, MN (US); Jason P. Hill, Brooklyn Park, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 253 days.

(21) Appl. No.: 13/253,497

(22) Filed: Oct. 5, 2011

(65) Prior Publication Data

US 2012/0158044 A1 Jun. 21, 2012

Related U.S. Application Data

(60) Provisional application No. 61/424,230, filed on Dec. 17, 2010.

(51) Int. Cl.
*A61B 17/08* (2006.01)

(52) U.S. Cl.
USPC ............................................ 606/213; 606/215

(58) Field of Classification Search
USPC ......... 606/191, 192, 194, 195, 198, 213, 215, 606/216, 232; 604/15, 16, 18, 60, 61
See application file for complete search history.

(56) References Cited

U.S. PATENT DOCUMENTS

| | | |
|---|---|---|
| 5,021,059 A | 6/1991 | Kensey et al. |
| 5,108,421 A | 4/1992 | Fowler |
| 5,129,882 A | 7/1992 | Weldon et al. |
| 5,192,300 A | 3/1993 | Fowler |
| 5,192,302 A | 3/1993 | Kensey et al. |
| 5,221,259 A | 6/1993 | Weldon et al. |
| 5,222,974 A | 6/1993 | Kensey et al. |
| 5,254,105 A | 10/1993 | Haaga |
| 5,275,616 A | 1/1994 | Fowler |
| 5,282,827 A | 2/1994 | Kensey et al. |
| 5,290,310 A | 3/1994 | Makower et al. |
| 5,292,332 A | 3/1994 | Lee |
| 5,310,407 A | 5/1994 | Casale |
| 5,312,435 A | 5/1994 | Nash et al. |
| 5,320,639 A | 6/1994 | Rudnick |
| 5,342,393 A | 8/1994 | Stack |
| 5,350,399 A | 9/1994 | Erlebacher et al. |
| 5,360,440 A | 11/1994 | Andersen |

(Continued)

FOREIGN PATENT DOCUMENTS

| EP | 1568326 A1 | 8/2005 |
|---|---|---|
| EP | 1671591 A1 | 6/2006 |

(Continued)

OTHER PUBLICATIONS

Loffler, Jorg F., et al., "MgZnCa Glasses without Clinically Observable Hydrogen Evolution for Biodegradable Inputs," Nature Materials, 3:887-891 (Nov. 2009). On-line at www.nature.com/naturematerials.

*Primary Examiner* — Dianne Dornbusch
*Assistant Examiner* — Robert Lynch
(74) *Attorney, Agent, or Firm* — Seager, Tufte & Wickhem LLC

(57) ABSTRACT

The present disclosure relates generally to methods and devices for closing and/or sealing an opening in a vessel wall and/or an adjacent tissue tract. In one illustrative embodiment, a device is provided for delivering and deploying an anchor, plug, suture, and/or locking element adjacent to the opening in the vessel wall and/or tissue tract.

17 Claims, 19 Drawing Sheets

(56) References Cited

U.S. PATENT DOCUMENTS

| | | |
|---|---|---|
| 5,370,660 A | 12/1994 | Weinstein et al. |
| 5,383,896 A | 1/1995 | Gershony et al. |
| 5,383,899 A | 1/1995 | Hammerslag |
| 5,391,183 A | 2/1995 | Janzen et al. |
| 5,411,520 A | 5/1995 | Nash et al. |
| 5,413,571 A | 5/1995 | Katsaros et al. |
| 5,415,657 A | 5/1995 | Taymor-Luria |
| 5,419,765 A | 5/1995 | Weldon et al. |
| 5,437,631 A | 8/1995 | Janzen |
| 5,441,517 A | 8/1995 | Kensey et al. |
| 5,443,481 A | 8/1995 | Lee |
| 5,447,502 A | 9/1995 | Haaga |
| 5,454,833 A | 10/1995 | Boussignac et al. |
| 5,478,326 A | 12/1995 | Shiu |
| 5,478,352 A | 12/1995 | Fowler |
| 5,486,195 A | 1/1996 | Myers et al. |
| 5,490,859 A | 2/1996 | Mische et al. |
| 5,501,694 A | 3/1996 | Ressemann et al. |
| 5,529,577 A | 6/1996 | Hammerslag |
| 5,531,759 A | 7/1996 | Kensey et al. |
| 5,540,707 A | 7/1996 | Ressemann et al. |
| 5,540,715 A | 7/1996 | Katsaros et al. |
| 5,545,178 A | 8/1996 | Kensey et al. |
| 5,549,633 A | 8/1996 | Evans et al. |
| 5,571,181 A | 11/1996 | Li |
| 5,573,518 A | 11/1996 | Haaga |
| 5,591,204 A | 1/1997 | Janzen et al. |
| 5,593,422 A | 1/1997 | Muijs Van de Moer et al. |
| 5,601,602 A | 2/1997 | Fowler |
| 5,613,974 A | 3/1997 | Andreas et al. |
| 5,620,461 A | 4/1997 | Muijs Van de Moer et al. |
| 5,626,601 A | 5/1997 | Gershony et al. |
| 5,630,833 A | 5/1997 | Katsaros et al. |
| 5,649,959 A | 7/1997 | Hannam et al. |
| 5,653,730 A | 8/1997 | Hammerslag |
| 5,662,681 A | 9/1997 | Nash et al. |
| 5,676,689 A | 10/1997 | Kensey et al. |
| 5,700,277 A | 12/1997 | Nash et al. |
| 5,707,393 A | 1/1998 | Kensey et al. |
| 5,716,375 A | 2/1998 | Fowler |
| 5,725,498 A | 3/1998 | Janzen et al. |
| 5,725,551 A | 3/1998 | Myers et al. |
| 5,728,114 A | 3/1998 | Evans et al. |
| 5,728,122 A | 3/1998 | Leschinsky et al. |
| 5,728,133 A | 3/1998 | Kontos |
| 5,728,134 A | 3/1998 | Barak |
| 5,741,223 A | 4/1998 | Janzen et al. |
| 5,782,860 A | 7/1998 | Epstein et al. |
| 5,810,884 A | 9/1998 | Kim |
| 5,830,130 A | 11/1998 | Janzen et al. |
| 5,836,868 A | 11/1998 | Ressemann et al. |
| 5,843,124 A | 12/1998 | Hammerslag |
| 5,853,421 A | 12/1998 | Leschinsky et al. |
| 5,861,004 A | 1/1999 | Kensey et al. |
| 5,871,474 A | 2/1999 | Hermann et al. |
| 5,871,501 A | 2/1999 | Leschinsky et al. |
| 5,897,567 A | 4/1999 | Ressemann et al. |
| 5,906,631 A | 5/1999 | Imran |
| 5,916,236 A | 6/1999 | Muijs Van de Moer et al. |
| 5,922,009 A | 7/1999 | Epstein et al. |
| 5,935,147 A | 8/1999 | Kensey et al. |
| 5,947,997 A | 9/1999 | Pavcnik et al. |
| 5,948,425 A | 9/1999 | Janzen et al. |
| 5,951,583 A | 9/1999 | Jensen et al. |
| 5,957,952 A | 9/1999 | Gershony et al. |
| 6,007,561 A | 12/1999 | Bourque et al. |
| 6,017,359 A | 1/2000 | Gershony et al. |
| 6,045,569 A | 4/2000 | Kensey et al. |
| 6,045,570 A | 4/2000 | Epstein et al. |
| 6,048,357 A | 4/2000 | Kontos |
| 6,048,358 A | 4/2000 | Barak |
| 6,054,569 A | 4/2000 | Bennett et al. |
| 6,056,768 A | 5/2000 | Cates et al. |
| 6,056,769 A | 5/2000 | Epstein et al. |
| 6,056,770 A | 5/2000 | Epstein et al. |
| 6,080,183 A | 6/2000 | Tsugita et al. |
| 6,110,184 A | 8/2000 | Weadock |
| 6,120,524 A | 9/2000 | Taheri |
| 6,126,675 A | 10/2000 | Shchervinsky et al. |
| 6,162,240 A | 12/2000 | Cates et al. |
| 6,179,863 B1 | 1/2001 | Kensey et al. |
| 6,183,496 B1 | 2/2001 | Urbanski |
| 6,190,400 B1 | 2/2001 | Van de Moer et al. |
| 6,261,309 B1 | 7/2001 | Urbanski |
| 6,287,332 B1 | 9/2001 | Bolz et al. |
| 6,296,632 B1 | 10/2001 | Luscher et al. |
| 6,296,657 B1 | 10/2001 | Brucker |
| 6,296,658 B1 | 10/2001 | Gershony et al. |
| 6,306,243 B1 | 10/2001 | Clark et al. |
| 6,325,789 B1 | 12/2001 | Janzen et al. |
| 6,350,274 B1 | 2/2002 | Li |
| 6,368,300 B1 | 4/2002 | Fallon et al. |
| 6,368,341 B1 | 4/2002 | Abrahamson |
| 6,425,911 B1 | 7/2002 | Akerfeldt et al. |
| 6,461,346 B1 | 10/2002 | Buelna |
| 6,464,712 B1 | 10/2002 | Epstein et al. |
| 6,468,293 B2 | 10/2002 | Bonutti et al. |
| 6,475,177 B1 | 11/2002 | Suzuki |
| 6,475,230 B1 | 11/2002 | Bonutti et al. |
| 6,500,152 B1 | 12/2002 | Illi |
| 6,508,828 B1 | 1/2003 | Akerfeldt et al. |
| 6,524,328 B2 | 2/2003 | Levinson |
| 6,527,734 B2 | 3/2003 | Cragg et al. |
| 6,537,299 B1 | 3/2003 | Hogendijk et al. |
| 6,540,735 B1 | 4/2003 | Ashby et al. |
| 6,569,187 B1 | 5/2003 | Bonutti et al. |
| 6,572,635 B1 | 6/2003 | Bonutti et al. |
| 6,592,608 B2 | 7/2003 | Fisher et al. |
| 6,596,012 B2 | 7/2003 | Akerfeldt et al. |
| 6,596,014 B2 | 7/2003 | Levinson et al. |
| 6,613,070 B2 | 9/2003 | Redmond et al. |
| 6,623,509 B2 | 9/2003 | Ginn |
| 6,632,238 B2 | 10/2003 | Ginn et al. |
| 6,656,207 B2 | 12/2003 | Epstein et al. |
| 6,663,650 B2 | 12/2003 | Sepetka et al. |
| 6,663,655 B2 | 12/2003 | Ginn et al. |
| 6,682,489 B2 | 1/2004 | Tenerz et al. |
| 6,685,727 B2 | 2/2004 | Fisher et al. |
| 6,699,261 B1 | 3/2004 | Cates et al. |
| 6,712,837 B2 | 3/2004 | Åkerfeldt et al. |
| 6,733,515 B1 | 5/2004 | Edwards et al. |
| 6,743,195 B2 | 6/2004 | Zucker |
| 6,749,621 B2 | 6/2004 | Pantages et al. |
| 6,764,500 B1 | 7/2004 | Muijs Van de Moer et al. |
| 6,780,197 B2 | 8/2004 | Roe et al. |
| 6,790,220 B2 | 9/2004 | Morris et al. |
| 6,818,008 B1 | 11/2004 | Cates et al. |
| 6,824,545 B2 | 11/2004 | Sepetka et al. |
| 6,860,895 B1 | 3/2005 | Akerfeldt et al. |
| 6,863,680 B2 | 3/2005 | Ashby |
| 6,890,342 B2 | 5/2005 | Zhu et al. |
| 6,890,343 B2 | 5/2005 | Ginn et al. |
| 6,896,692 B2 | 5/2005 | Ginn et al. |
| 6,929,655 B2 | 8/2005 | Egnelov et al. |
| 6,939,363 B2 | 9/2005 | Åkerfeldt |
| 6,942,684 B2 | 9/2005 | Bonutti |
| 6,955,683 B2 | 10/2005 | Bonutti |
| 6,964,658 B2 | 11/2005 | Ashby et al. |
| 6,969,397 B2 | 11/2005 | Ginn |
| 7,001,398 B2 | 2/2006 | Carley et al. |
| 7,008,439 B1 | 3/2006 | Janzen et al. |
| 7,008,440 B2 | 3/2006 | Sing et al. |
| 7,008,441 B2 | 3/2006 | Zucker |
| 7,008,442 B2 | 3/2006 | Brightbill |
| 7,025,776 B1 | 4/2006 | Houser et al. |
| 7,037,323 B2 | 5/2006 | Sing et al. |
| 7,044,916 B2 | 5/2006 | Tenerz et al. |
| 7,083,635 B2 | 8/2006 | Ginn |
| 7,192,436 B2 | 3/2007 | Sing et al. |
| 7,250,057 B2 | 7/2007 | Forsberg |
| 7,267,679 B2 | 9/2007 | McGuckin, Jr. et al. |
| 7,285,126 B2 | 10/2007 | Sepetka et al. |
| 7,316,704 B2 | 1/2008 | Bagaoisan et al. |
| 7,322,976 B2 | 1/2008 | Yassinzadeh |

(56) References Cited

U.S. PATENT DOCUMENTS

| | | |
|---|---|---|
| 7,331,979 B2 | 2/2008 | Khosravi et al. |
| 7,331,981 B2 | 2/2008 | Cates et al. |
| 7,335,220 B2 | 2/2008 | Khosravi et al. |
| 7,344,544 B2 | 3/2008 | Bender et al. |
| 7,527,637 B2 | 5/2009 | Sater et al. |
| 7,534,252 B2 | 5/2009 | Sepetka et al. |
| 7,618,436 B2 | 11/2009 | Forsberg |
| 7,618,438 B2 | 11/2009 | White et al. |
| 7,686,825 B2 | 3/2010 | Hauser et al. |
| 7,691,127 B2 | 4/2010 | Yassinzadeh |
| 7,713,283 B2 | 5/2010 | Forsberg |
| 7,731,726 B2 | 6/2010 | Belhe et al. |
| 7,749,247 B2 | 7/2010 | Tegg |
| 7,749,248 B2 | 7/2010 | White et al. |
| 2002/0002889 A1 | 1/2002 | Ashby et al. |
| 2002/0016612 A1 | 2/2002 | Ashby et al. |
| 2002/0072768 A1 | 6/2002 | Ginn |
| 2002/0133123 A1 | 9/2002 | Zucker et al. |
| 2002/0198562 A1 | 12/2002 | Akerfeldt et al. |
| 2003/0023267 A1 | 1/2003 | Ginn |
| 2003/0055454 A1 | 3/2003 | Zucker et al. |
| 2003/0088271 A1 | 5/2003 | Cragg et al. |
| 2004/0073243 A1 | 4/2004 | Sepetka et al. |
| 2004/0093025 A1 | 5/2004 | Egnelov |
| 2004/0098025 A1 | 5/2004 | Sepetka et al. |
| 2004/0098044 A1 | 5/2004 | Muijs Van de Moer et al. |
| 2004/0098046 A1 | 5/2004 | Tenerz et al. |
| 2004/0172059 A1 | 9/2004 | Tenerz et al. |
| 2004/0204741 A1 | 10/2004 | Egnelov et al. |
| 2004/0215232 A1 | 10/2004 | Belhe et al. |
| 2004/0243007 A1 | 12/2004 | Tenerz et al. |
| 2005/0049619 A1 | 3/2005 | Sepetka et al. |
| 2005/0049637 A1 | 3/2005 | Morris et al. |
| 2005/0085851 A1 | 4/2005 | Fiehler et al. |
| 2005/0085852 A1 | 4/2005 | Ditter |
| 2005/0085855 A1 | 4/2005 | Forsberg |
| 2005/0085856 A1 | 4/2005 | Ginn |
| 2005/0096696 A1 | 5/2005 | Forsberg |
| 2005/0096697 A1 | 5/2005 | Forsberg et al. |
| 2005/0107827 A1 | 5/2005 | Paprocki |
| 2005/0121042 A1 | 6/2005 | Belhe et al. |
| 2005/0125031 A1 | 6/2005 | Pipenhagen et al. |
| 2005/0137624 A1 | 6/2005 | Fallman |
| 2005/0169974 A1 | 8/2005 | Tenerz et al. |
| 2005/0177189 A1 | 8/2005 | Ginn et al. |
| 2005/0220837 A1 | 10/2005 | Disegi et al. |
| 2005/0261760 A1 | 11/2005 | Weber |
| 2005/0267521 A1 | 12/2005 | Forsberg |
| 2005/0267528 A1 | 12/2005 | Ginn et al. |
| 2005/0267560 A1 | 12/2005 | Bates |
| 2006/0004408 A1 | 1/2006 | Morris et al. |
| 2006/0030886 A1 | 2/2006 | Clark |
| 2006/0034930 A1 | 2/2006 | Khosravi et al. |
| 2006/0047313 A1 | 3/2006 | Khanna et al. |
| 2006/0052825 A1 | 3/2006 | Ransick et al. |
| 2006/0058844 A1 | 3/2006 | White et al. |
| 2006/0064124 A1 | 3/2006 | Zhu et al. |
| 2006/0100664 A1 | 5/2006 | Pai et al. |
| 2006/0142797 A1 | 6/2006 | Egnelov |
| 2006/0173492 A1 | 8/2006 | Akerfeldt et al. |
| 2006/0178682 A1 | 8/2006 | Boehlke |
| 2006/0195137 A1 | 8/2006 | Sepetka et al. |
| 2006/0206146 A1 | 9/2006 | Tenerz |
| 2006/0217744 A1 | 9/2006 | Bender et al. |
| 2006/0229662 A1 | 10/2006 | Finkielsztein et al. |
| 2006/0229664 A1 | 10/2006 | Finkielsztein et al. |
| 2006/0229672 A1 | 10/2006 | Forsberg |
| 2006/0229673 A1 | 10/2006 | Forsberg |
| 2006/0229674 A1 | 10/2006 | Forsberg |
| 2006/0265006 A1 | 11/2006 | White et al. |
| 2006/0265007 A1 | 11/2006 | White et al. |
| 2006/0265008 A1 | 11/2006 | Maruyama et al. |
| 2007/0032823 A1 | 2/2007 | Tegg |
| 2007/0032824 A1 | 2/2007 | Terwey |
| 2007/0038244 A1 | 2/2007 | Morris et al. |
| 2007/0038245 A1 | 2/2007 | Morris et al. |
| 2007/0073345 A1 | 3/2007 | Pipenhagen et al. |
| 2007/0083231 A1 | 4/2007 | Lee |
| 2007/0083232 A1 | 4/2007 | Lee |
| 2007/0135837 A1 | 6/2007 | Yassinzadeh |
| 2007/0135842 A1 | 6/2007 | Muijs Van de Moer et al. |
| 2007/0208371 A1 | 9/2007 | French et al. |
| 2007/0219576 A1 | 9/2007 | Cangialosi |
| 2007/0219623 A1 | 9/2007 | Palmaz |
| 2007/0270942 A1 | 11/2007 | Thomas |
| 2007/0276433 A1 | 11/2007 | Huss |
| 2008/0065121 A1 | 3/2008 | Kawaura et al. |
| 2008/0071311 A1 | 3/2008 | White et al. |
| 2008/0071350 A1 | 3/2008 | Stinson |
| 2008/0097521 A1 | 4/2008 | Khosravi et al. |
| 2008/0109030 A1 | 5/2008 | Houser et al. |
| 2008/0109031 A1 | 5/2008 | Sepetka et al. |
| 2008/0114394 A1 | 5/2008 | Houser et al. |
| 2008/0188876 A1 | 8/2008 | Sepetka et al. |
| 2008/0200600 A1 | 8/2008 | Schomaker et al. |
| 2008/0215077 A1 | 9/2008 | Sepetka et al. |
| 2008/0234706 A1 | 9/2008 | Sepetka et al. |
| 2008/0262532 A1 | 10/2008 | Martin |
| 2009/0024106 A1 | 1/2009 | Morris |
| 2009/0069828 A1 | 3/2009 | Martin et al. |
| 2009/0143789 A1 | 6/2009 | Houser |
| 2009/0299393 A1 | 12/2009 | Martin et al. |
| 2010/0023051 A1 | 1/2010 | White et al. |
| 2010/0191280 A1 | 7/2010 | Forsberg |
| 2010/0217311 A1 | 8/2010 | Jenson et al. |
| 2010/0234883 A1 | 9/2010 | White et al. |
| 2010/0286727 A1* | 11/2010 | Terwey .................. 606/213 |
| 2011/0029012 A1* | 2/2011 | Tegels .................. 606/213 |

FOREIGN PATENT DOCUMENTS

| | | |
|---|---|---|
| WO | 8911301 A1 | 11/1989 |
| WO | 9922646 A1 | 5/1999 |
| WO | 02053202 A1 | 7/2002 |
| WO | 2006078578 A2 | 7/2006 |
| WO | 2006124238 A2 | 11/2006 |
| WO | 2006124251 A2 | 11/2006 |
| WO | 2009025836 A1 | 2/2009 |
| WO | 20091008750 A1 | 9/2009 |
| WO | 2010056915 A1 | 5/2010 |
| WO | 2010129042 A1 | 11/2010 |
| WO | 2011100547 A2 | 8/2011 |

* cited by examiner

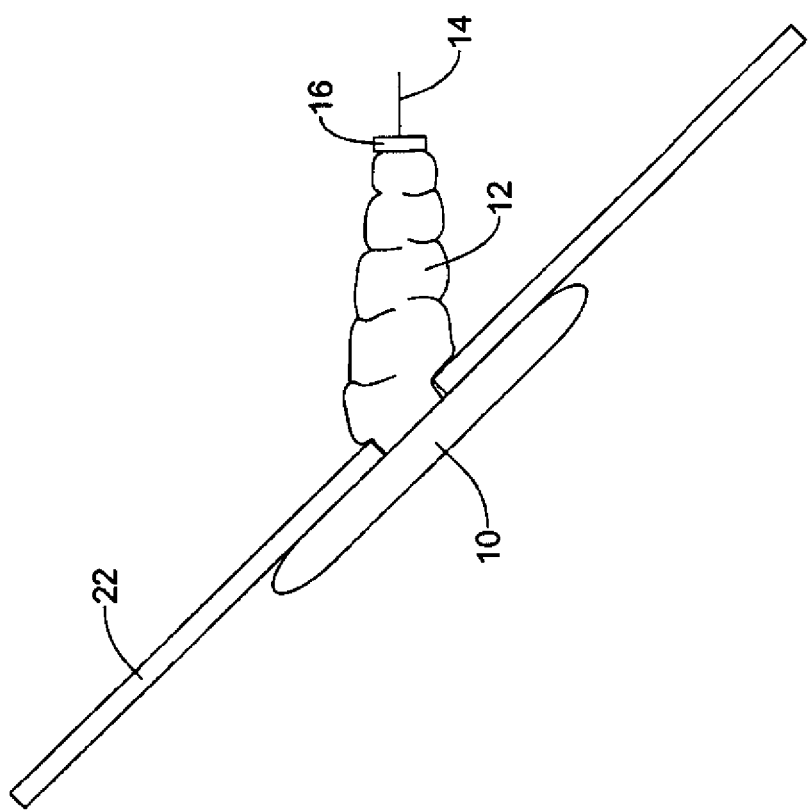

TISSUE PUNCTURE CLOSURE DEVICE

RELATED APPLICATIONS

This application claims priority to U.S. Provisional Application Ser. No. 61/424,230 filed Dec. 17, 2010.

FIELD

The present disclosure relates generally to medical devices and more particularly to methods and devices for closing and/or sealing punctures in tissue.

BACKGROUND

In many medical procedures, such as, for example, balloon angioplasty and the like, an opening can be created in a blood vessel or arteriotomy to allow for the insertion of various medical devices which can be navigated through the blood vessel to the site to be treated. For example, after initial access with a hollow needle, a guidewire may first be inserted through the tissue tract created between the skin, or the epidermis, of the patient down through the subcutaneous tissue and into the opening formed in the blood vessel. Once the guidewire is in place, an introducer sheath can be slid over the guide wire to form a wider, more easily accessible, tract between the epidermis and the opening into the blood vessel. The appropriate medical device can then be introduced through the introducer sheath and then up the blood vessel to the site of the occlusion or other treatment site.

Once the procedure is completed, the medical devices or other equipment introduced into the vessel can be retracted through the blood vessel, out the opening in the blood vessel wall, and out through the tissue tract to be removed from the body. The physician or other medical technician is presented with the challenge of trying to close the opening in the blood vessel and/or the tissue tract formed in the epidermis and subcutaneous tissue. A number of different device structures, assemblies, and methods are known for closing the opening in the blood vessel and/or tissue tract, each having certain advantages and disadvantages. However, there is an ongoing need to provide new and improved device structures, assemblies, and/or methods for closing and/or sealing the opening in the blood vessel and/or tissue tract.

BRIEF SUMMARY

The following summary is provided to facilitate an understanding of some of the innovative features unique to the present disclosure and is not intended to be a full description. A full appreciation of the disclosure can be gained by taking the entire specification, claims, drawings, and abstract as a whole.

The present disclosure relates generally to medical devices and more particularly to methods and devices for closing and/or sealing punctures in tissue. In one illustrative embodiment, a device is provided for delivering and deploying an anchor, plug, suture, and a locking element adjacent to the opening in the vessel wall and/or tissue tract. In some cases, the plug may be configured to compress against the anchor when deployed in the tissue tract and/or opening in the vessel wall. In some cases, the suture may be automatically released from the device when the plug is compressed. In some cases, the device may include a motor to facilitate controlled, automatic compression of the plug.

BRIEF DESCRIPTION OF THE DRAWINGS

The disclosure may be more completely understood in consideration of the following detailed description of various embodiments of the invention in connection with the accompanying drawings, in which:

FIGS. 11-19 are partial cut-away schematic diagrams of an illustrative implantation device that may be used in the procedure of FIGS. 1-10.

Figure 1:
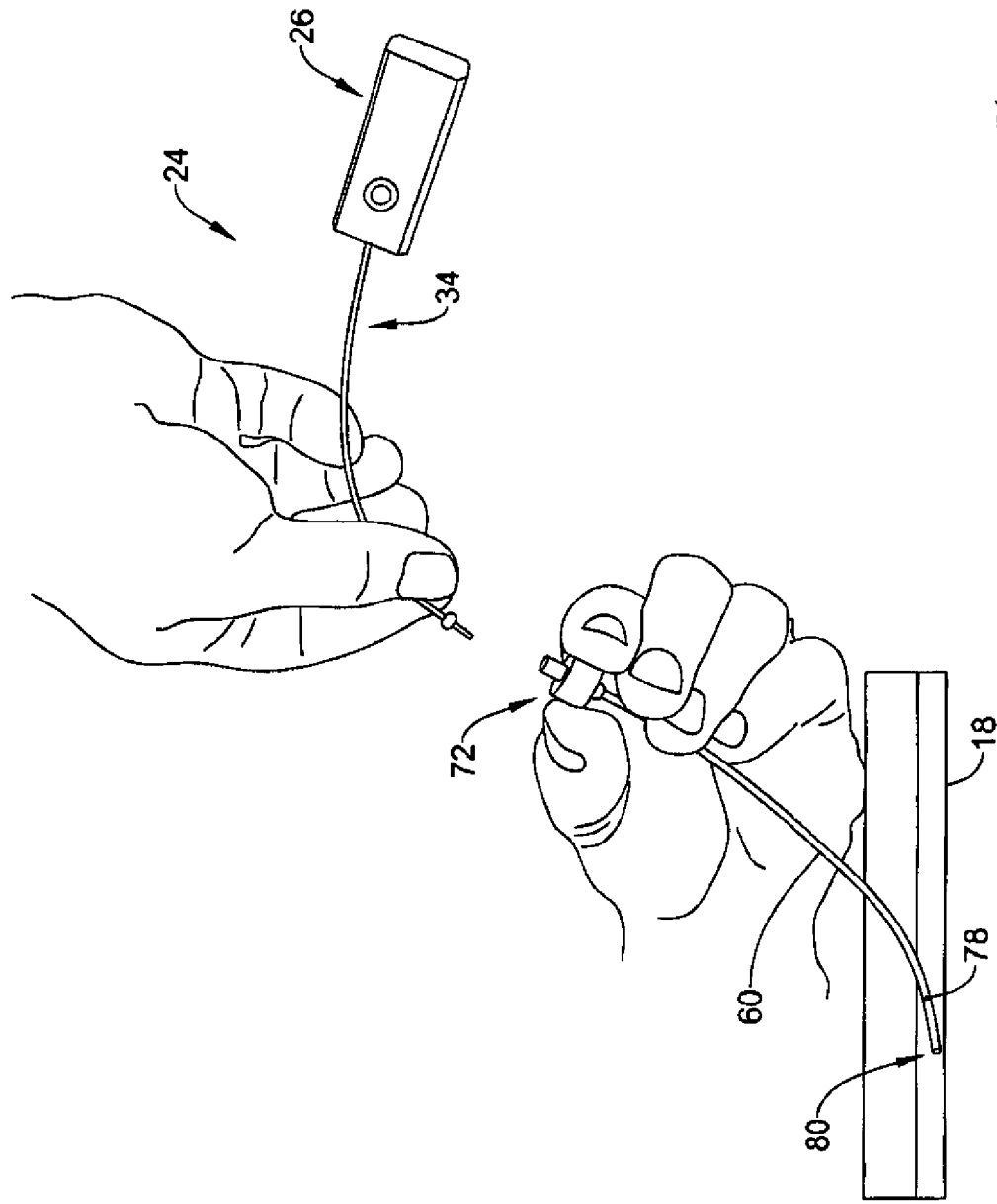
FIG. 1-10 are perspective views and partial cut-away perspective views showing an illustrative procedure for sealing and/or closing a puncture in a vessel wall and/or adjacent tissue tract.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

FIGS. 1-10 are perspective views and partial cut-away perspective views showing an illustrative procedure for sealing and/or closing a puncture in a vessel wall 22 and/or adjacent tissue tract 20 using an illustrative implantation device 24. In some cases, a medical procedure can be performed with a procedural sheath, which in some cases, may be different than the insertion sheath 60 described herein. In some cases, a guidewire (not shown) may be used to facilitate insertion of the insertion sheath 60 and/or the implantation device 24. A mating dilator (not shown) may be provided to support the insertion sheath 60 during advancement over the guidewire. In some cases, the vessel may be occluded by depressing the skin to temporarily stop the flow of blood therethrough.

A suitable bleed path position indicator may be used to correctly position a distal end of the insertion sheath 60 in the blood vessel 18. In some embodiments, at least one opening 78 in the insertion sheath 60 may define an entrance to a bleed path that may be used to determine if the distal end of the insertion sheath 60 is located within the lumen of the blood vessel 18. In some cases, the opening(s) 78 may be aligned with and fluidly communicate with a dilator (not shown). Blood may enter the bleed path through the distal opening(s) 78 and move proximally within the dilator (not shown). Blood moving through the bleed path may leak from a proximal bleed hole (not shown) in the dilator, thereby indicating the distal end of the insertion sheath 60 is disposed within the blood vessel 18. Once the proper position is located, the dilator (not shown), if used, may be removed and the device sheath 34 may be inserted into the insertion sheath 60, as shown in FIG. 1. However, other suitable position indicators and/or locators may be used, such as, for example, one or more bent wires, one or more interlocking buttons, one or more folded components, an inflatable balloon, a radially expanding disc, as well as other suitable position indicator and/or locator or combination thereof, as desired.

In some embodiments, the insertion sheath 60 may be maintained in the located position during and/or after removal of the dilator (not shown) or other position indicator. In some cases, an annular shaped locking ring or other suitable locking ring, such as an elastomeric o-ring, can be used to maintain the position of the insertion sheath 60. In other cases, a physician or medical technician may hold the insertion sheath 60 to maintain the position. In some embodiments, an indicator or other visual mark can be provided to verify that the proper location is maintained. In some cases, the insertion sheath 60 may include an orientation indicator (not shown) on a proximal end thereof to help orient the insertion sheath 60. In some cases, the orientation indicator may be a line, mark, shape, other indicator, or combination thereof, to aid a user in orienting the insertion sheath 60 relative to its position in the vessel. The implantation device 24 can then be inserted into the proximal end of the insertion sheath 60, as shown in FIG. 1. In some embodiments, insertion sheath 60 can include a hemostatic valve disposed therein. The implantation device 24 can be inserted through the hemostatic valve and connected to the insertion sheath 60. At the same time, an anchor 10 can be introduced into the vessel 18.

Implantation device 24 may include an anchor 10, a plug 12, a suture 14, and a locking element 16 for closing and/or sealing an opening in a blood vessel 18 and/or adjacent tissue tract 20 that was created to gain access to the vessel 18 to perform a medical procedure. The anchor 10 may be configured to engage an interior surface of the vessel wall 22. In some cases, the anchor 10 may be configured to partially or completely occlude the opening in the vessel wall 22, as desired. The anchor 10 may include a biodegradable material so that, over time, the anchor 10 is degraded, eroded, and/or absorbed in the body. In some cases, the anchor 10 may include a PLGA, PLLA, PGA or other degradable or erodable polymers, such as polyesters, polysaccharides, polyanhydrides, polycaprolactone, and various combinations thereof. In some cases, the anchor 10 may include a combination of the previously mentioned materials to impart a variable strength and/or degradation time profile in the anchor 10. One example anchor 10 that is configured to rapidly absorb and/or degrade is disclosed in Application Ser. No. 61/031,456, filed Feb. 26, 2008, which is hereby incorporated by reference. However, it is contemplated that other suitable anchors 10 may be used, as desired.

Suture 14 may include a proximal end, a distal end, and a length extending therebetween. The distal end of the suture 14 may be coupled to the anchor 10 with the suture 14 extending proximally therefrom. In some cases, the anchor 10 may include a raised portion including an eyelet to facilitate attachment of the distal end of the suture 14 to the anchor.

The suture 14 may include a biodegradable material so that, over time, the suture 14 is degraded, eroded, and/or absorbed in the body. In some cases, the suture 14 may include a PLGA, PLLA, PGA or other degradable or erodable polymers, such as polyesters, polysaccharides, polyanhydrides, polycaprolactone, and various combinations thereof.

In the illustrative embodiment, the plug 12 can be disposed about at least a portion of the suture 14 adjacent to the anchor 10 in the tissue tract 20 and/or opening of the vessel wall 22. The plug 12 may be configured to fill the space in the tissue tract 20 adjacent to the vessel 18 and/or the opening in the vessel wall 22 to close and/or seal the vessel 18 opening and/or tissue tract 20. In some examples, the plug 12 may include a material that swells to fill space in the tissue tract 20 and/or vessel wall 22 opening, such as by elastic expansion, fluid absorption, chemical reaction, as well as other suitable swelling and/or expansion. The plug 12 can be configured to promote hemostasis and/or clotting adjacent to the vessel 18. In one example, the plug may include collagen foam, gelatin foam, PEG or other hydrogel, starch powder, other suitable hemostatic materials, other suitable clot-promoting materials, as well as other suitable materials, as desired. In some cases, other materials can be used to provide control of thrombogenicity or hydration.

In the illustrative embodiment, the plug 12 may be generally cylindrical in shape with a lumen extending therethrough. As illustrated, the plug 12 is shown in an axially compressed state after it has been deployed in the tissue tract 20. In some cases, the plug 12 can be radially compressed prior to delivery, as desired.

The plug 12 may include a biodegradable material so that, over time, the plug 12 is degraded, eroded, and/or absorbed in the body. In one example, the plug 12 can include an elongated member formed from collagen foam or gelatin foam, such as, for example, GELFOAM® (Pharmacia & Upjohn, Inc., Bridgewater, N.J.) or Surgifoam™ (Johnson & Johnson, New Brunswick, N.J.). In some cases, the plug 12 can also include a hydrogel and/or a hemostatic material, if desired. Example hydrogels can include polyethylene glycols (PEG), including PEG 900, PEG 3350, and PEG 6000, as well as other suitable hydrogels, as desired. Examples of hemostatic materials can include starch powders, such as BleedArrest™ Clotting Powder (Hemostasis, LLC, St. Paul, Minn.). In one illustrative example, the starch powder can be disposed in or on the collagen or gelatin foam. In this illustrative example, the hydrogel can be coated on at least a portion of the collagen or gelatin foam and starch powder combination by, for example, drip coating, spray coating, or dip coating. However, other suitable methods of combining the collagen or gelatin foam, hydrogel, and starch powder can be used, as desired.

Some examples of plugs and plug materials that may be used in the closure device are disclosed in co-pending application Ser. No. 12/390,289, filed on Feb. 20, 2009, which is hereby incorporated by reference. In some cases, the plug 12 can include one or more voids, notches, slits, or other modifications to provide a desired axial compression of plug 12. Examples of plugs that may include voids, notches, slits, or other modification are disclosed in co-pending application Ser. No. 12/389,960, filed on Feb. 20, 2009, which is hereby incorporated by reference. In some cases, the illustrative plug 12 can be processed to have desired expansion characteristics. For example, the plug 12 can be tenderized to break down cell walls to increase the rate of expansion of the plug 12. Examples of plugs that have been tenderized or otherwise processed and methods of tenderizing or otherwise processing are disclosed in co-pending application Ser. No. 12/390,067, filed on Feb. 20, 2009, which is hereby incorporated by reference.

In the illustrative embodiment, one or more locking elements 16 can be used to help secure the plug 12 relative to the anchor 10. As illustrated, the locking element 16 can be disposed about at least a portion of the suture 14 proximal of the anchor 10 and the plug 12. The locking element 16 can be configured to slide over the suture 14 and compress the plug 12 during deployment. In some cases, the locking element 16 can be slid distally over the suture 14 to compress the plug 12, maintaining the distal portion of the suture 14 under tension. In some cases, the locking element 16 can be a knot, such as a compression knot that may exert a radial force on the suture 14. As such, the knot may have a friction force of 0.5 pounds, 1 pound, 1.5 pounds, 2.0 pounds, 2.5 pounds, 3.0 pounds, or other suitable friction force depending on the production of the knot 16. In any event, the friction force of the knot 16 may be greater than the rebound force of the plug 12 to prevent the plug 12 from axially expanding after axial compression.

In an illustrative embodiment, the locking element 16 may be separate and independent from the suture 14. In some cases, the locking element 16 may include a filament that is independent of the suture 14. In some cases, the filament of the locking element 16 may have a larger radial diameter than the suture 14 so that the locking element 16 has a sufficient size to contact the proximal end of the plug 12 for axial compression without penetrating into the plug 12.

In other cases, the locking element 16 can be a sliding cinch, a disc shaped retainer, or other device. In some cases, the locking element 16 may be capable of sliding relative to the suture 14 upon an exertion of force. In other cases, the locking element 16 can be configured to slide in a distal direction relative to the suture 14, but not in a proximal direction. An example locking element is disclosed in co-pending application Ser. No. 12/389,847, filed on Feb. 20, 2009, which is hereby incorporated by reference.

The locking element 16 may include a biodegradable material so that, over time, the locking element 16 is degraded, eroded, and/or absorbed in the body. In some cases, the locking element 16 may include a PLGA, PLLA, PGA or other degradable or erodable polymers, such as polyesters, polysaccharides, polyanhydrides, polycaprolactone, and various combinations thereof.

Figure 13:
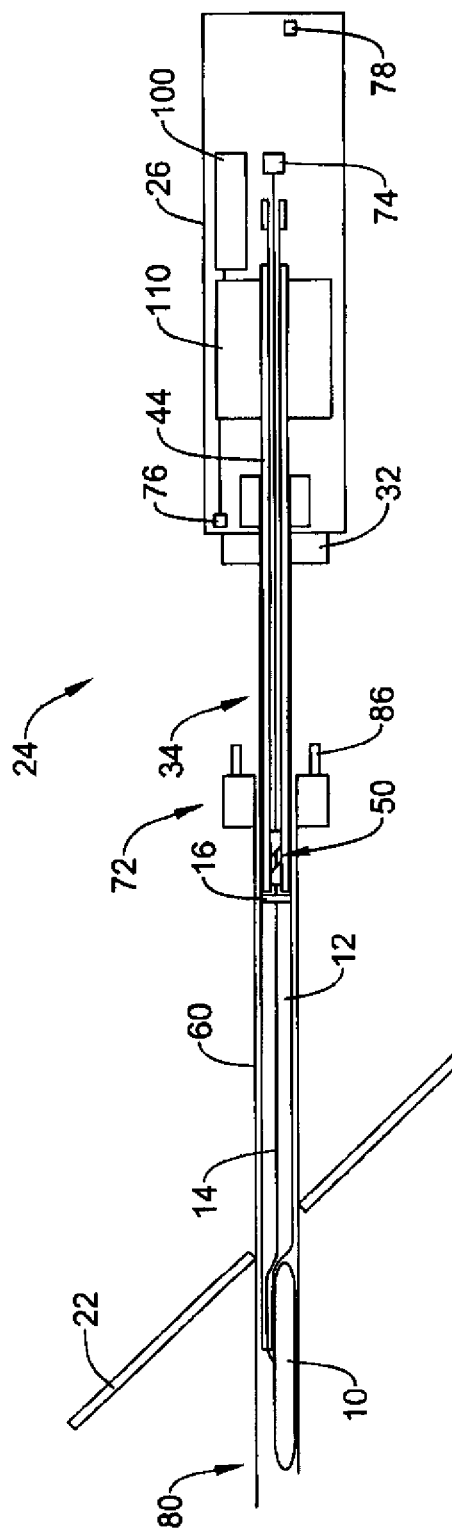
Figure 14:
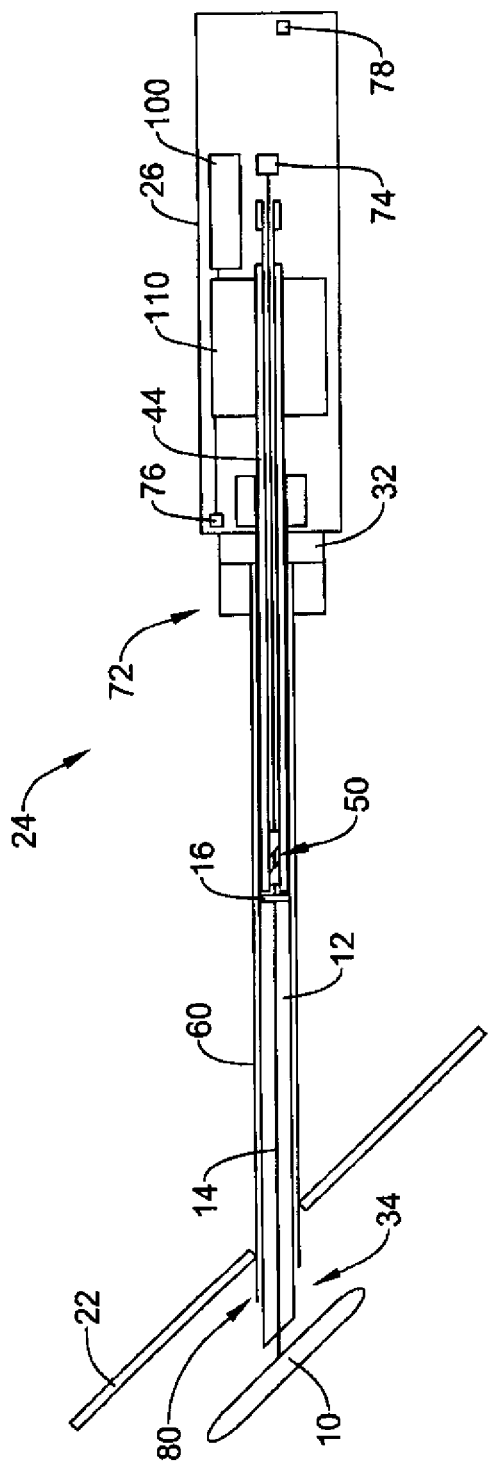

The implantation device 24 may include a device handle 26 and a device sheath 34. The device sheath 34 may be a tubular member having a proximal end fixedly coupled to the handle 26. The anchor 10 can be disposed adjacent the distal end of the device sheath 34, either within the device sheath 34, partially within the device sheath 34, or outside the device sheath 34. The anchor 10, when positioned outside the device sheath 34 generally in axial alignment with the device sheath 34, may at least partially deform the distal end of the device sheath 34 about the anchor 10, as seen in FIG. 13, for example. This arrangement permits the distal end of the plug 12 to be maintained in close proximity to the anchor 10, thereby minimizing any gap between the two elements. As the anchor 10 is positioned generally transverse to the distal end of the sheath, the deformed portion of the distal end of the device sheath 34 may assume a shape or form substantially similar to a proximal portion of the device sheath 34, as seen in FIG. 14, for example. The plug 12, suture 14, and locking element 16 can be disposed within the device sheath 34.

The device handle 26 may include a control handle connector 32 configured to attach the implantation device 24 to an insertion sheath 60. The illustrative implantation device 24 may allow for ambidextrous use and provide controlled deployment of the anchor 10, plug, 12, suture 14, and/or locking element 16.

In some embodiments, a push rod 44 can be provided having a proximal end disposed in the device handle 26 and a distal end disposed in the device sheath 34. A proximal end of the push rod 44 can be operatively coupled to a motor 110 within the handle 26, where the motor 110 is configured to adjust the relative relationship of the push rod 44 and handle 26 in response to the activation of a force trigger 78. Motor 110 may be operatively connected to an energy source and/or control system 100 disposed within the handle 26. Force trigger 78 may be operatively connected to control system 100 to provide an input thereto. The force trigger 78 may be activated by a predetermined tensile force applied when the anchor 10 is positioned against the wall 22 of the blood vessel 18 and the handle 26 is tensioned proximally away from the blood vessel 18. Alternatively, the force trigger 78 may be activated by an optional, manually-activated switch in communication with an exterior of the handle 26, where the optional, manually-activated switch may be actuated by a user of the implantation device 24. The optional, manually-activated switch is shown in the Figures, but need not be present in all embodiments. For example, embodiments utilizing an automatic or tensile force-activated force trigger may not have a separate manually-activated switch. However, it is contemplated that some embodiments may have an automatic force trigger and a manually-activated switch.

Figure 7:
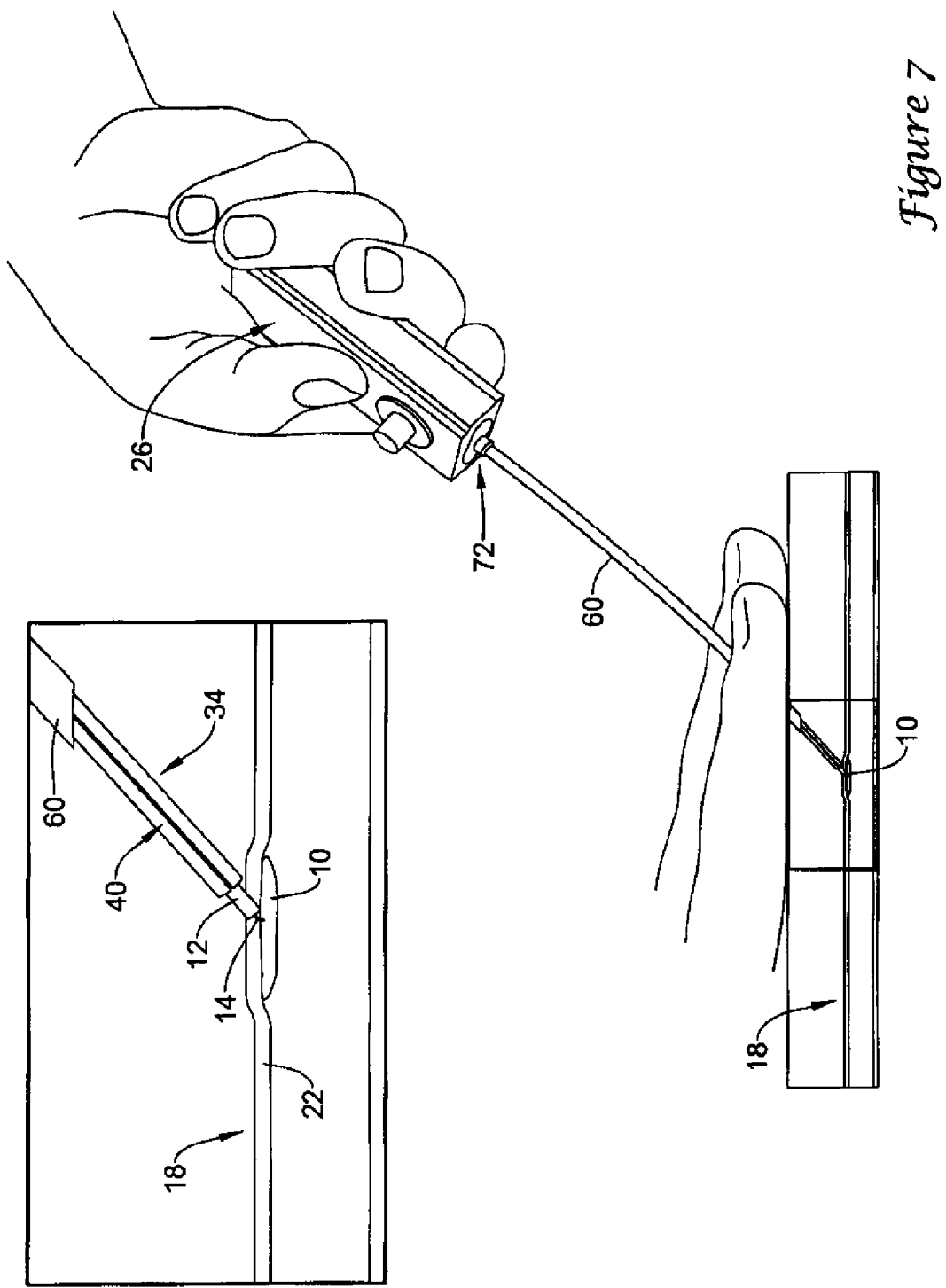
Figure 16:
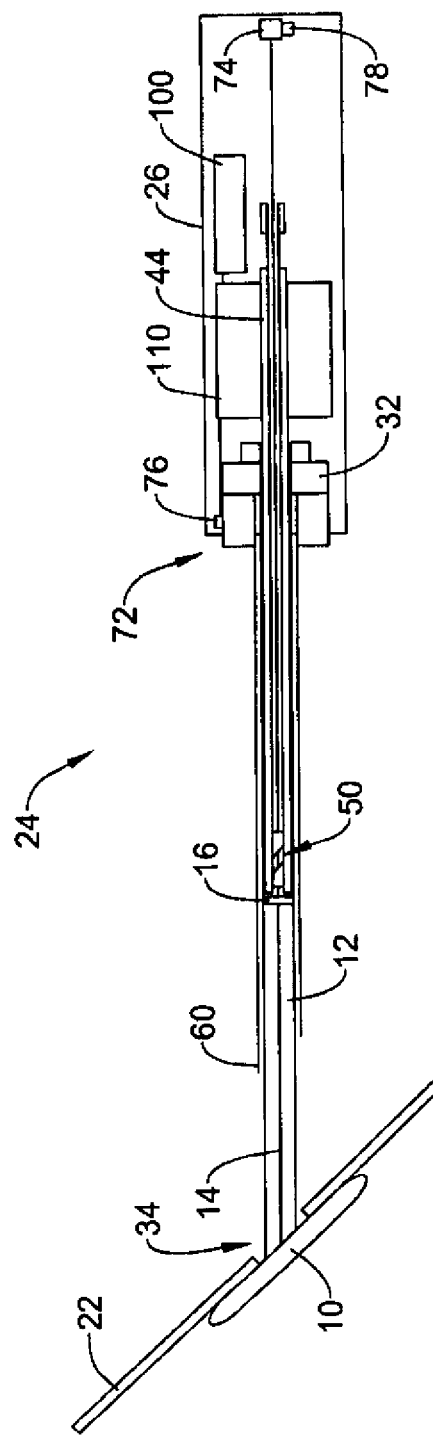

Activation of force trigger 78 may cause control handle connector 32, hub 72, and insertion sheath 60 to be withdrawn proximally relative to the anchor 10 to create a small gap for deployment of plug 12, as seen in FIGS. 7 and 16, for example. Withdrawal may be facilitated manually, by actuation of the motor 110, a spring mechanism, or other operatively connected means as appropriate. Device sheath 34 and the handle 26 remain fixed in position relative to the anchor 10. Following withdrawal of insertion sheath 60, motor 110 may be actuated manually, sequentially, or automatically to extend push rod 44 distally to deploy the plug 12.

Motor 110 may provide a controlled displacement and compression speed for deployment of the plug 12. A motor-driven system can reduce the forces applied by a user to the implantation device 24 during deployment, may provide gradual acceleration and deceleration of the compression movements within the device, and may reduce peak actuation forces to avoid damage to the plug 12 during compression or to avoid fracturing the anchor 10.

Figure 17:
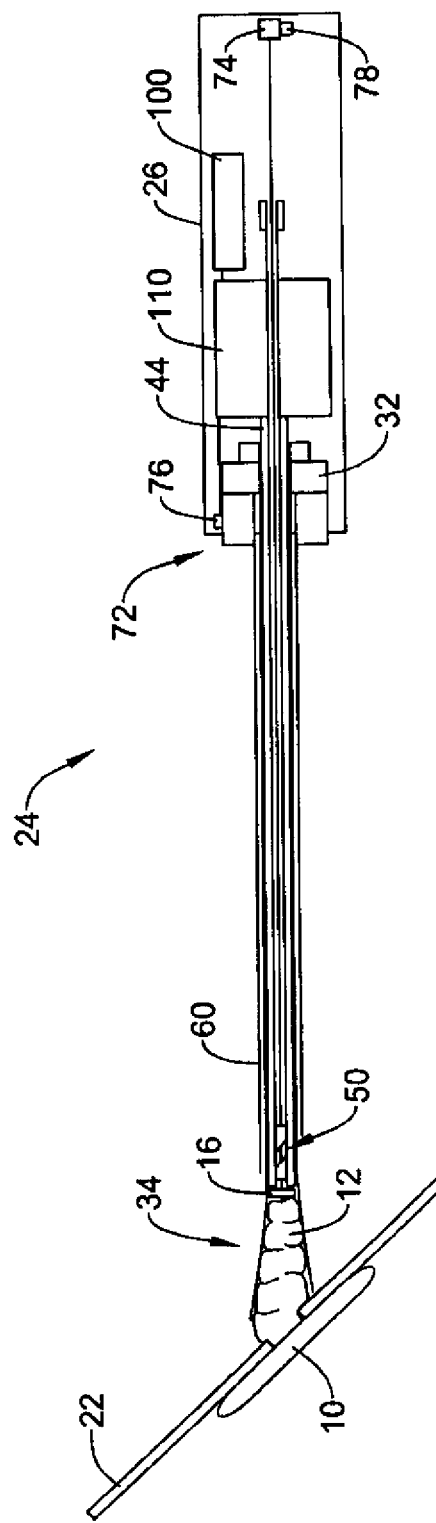
Figure 18:
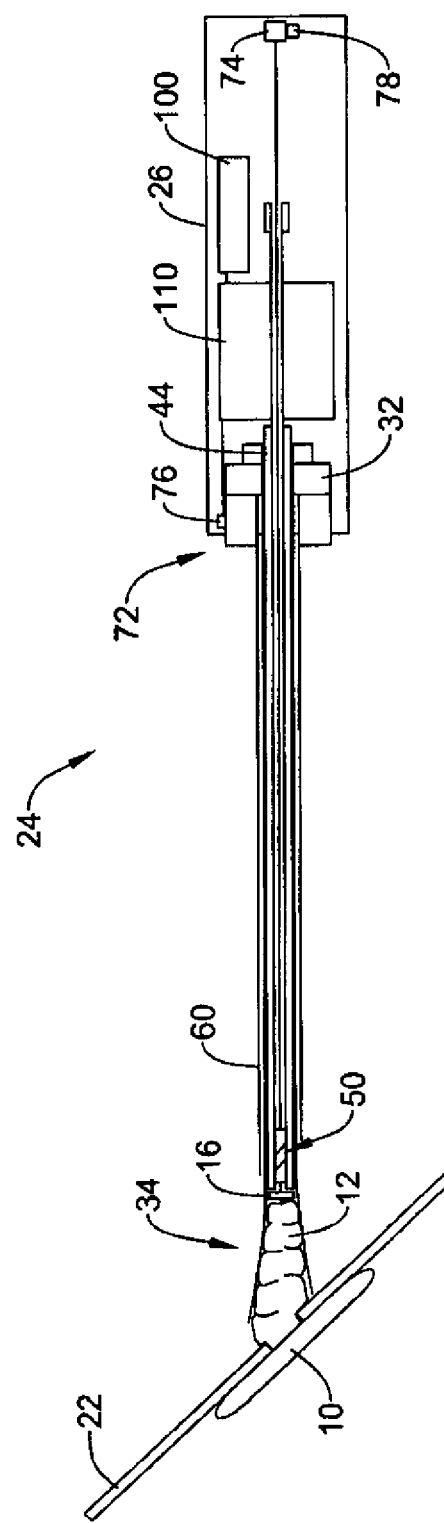

Push rod 44 may advance against the locking element 16 to compress the plug 12, as shown in FIG. 17. The plug 12 may be compressed and secured in the compressed state by the locking element 16. In one example, the locking element 16 may have a compressive force on the suture creating a friction force in the locking element of 0.5 pounds, 1 pound, 1.5 pounds, 2 pounds, or other suitable friction force, as desired. Accordingly, the force exerted by the push rod 44 onto the locking element 16 may be greater than the friction force between the locking element 16 and the suture 14. Further, the plug 12 may exert a rebounding force on the locking element 16 trying to return to the non-axially compressed position. However, the friction force of the locking element 16 may be configured to be greater than the rebounding force of the plug 12.

In some embodiments, the push rod 44 can include a suture release member 50 such as a collet, but other suitable push rods may be used, as desired. The distal end of the push rod 44 can include a collet lock ring that is configured to have a releasable engagement with the suture 14. In some cases, the distal end of the push rod 44 can be coupled to the suture 14. A release bead can be disposed about a portion of the push rod 44 a distance from the collet lock ring. The release bead may slide relative to the push rod 44 and is configured to engage the collet lock ring and slide the collet lock ring off of the distal end of the tubular member 44, releasing the suture 14.

A proximal tubular member can be disposed about at least a portion of the push rod 44 proximal of the release bead. A distal tubular member can be disposed about the push rod 44 and have a proximal end configured to engage the release bead and a distal end configured to engage locking element 16. The distal tubular member may be configured to slide over the collet lock ring. In some cases, the release bead may simultaneously or concurrently pass over the push rod 44 and engage the collet lock ring to automatically release the suture 14 from the implantation device 24. The push rod 44, proximal tubular member, release bead, distal tubular member, and collet lock ring may be disposed within the device sheath 34.

In some embodiments, the push rod 44 and/or the proximal tubular member and the distal tubular member may be a coil having a number of turns. However, it is contemplated that a suitable tubular member having a sufficient pushability and flexibility may be used, as desired.

In some embodiments, the suture 14 may include an attachment element such as a loop, disposed at the proximal end of the suture 14. The suture 14 may be released from the handle 26 by releasing the attachment element. The collet described herein may also be considered an attachment element, as releasing either element may result in the suture 14 being released from the handle 26.

In some embodiments, the suture release member 50 may include a cutting element configured to cut the suture 14 within the device sheath 34 following deployment of the plug 12 to release the suture 14 from the handle 26.

The implantation device 24 may also include a control handle connector 32 configured to engage a hub 72 of the insertion sheath 60. The control handle connector 32 can be configured to be housed in the distal end of the handle 26 or extend partially out of the distal end of the handle 26. The control handle connector 32 may include a lumen configured to receive a proximal region of the device sheath 34 such that the device sheath 34 may pass through the control handle connector 32.

Insertion sheath 60 may include a hub 72 configured to couple the insertion sheath 60 to the control handle connector 32. The hub 72 may include one or more pins and/or protrusions 86 that are configured to engage the control handle connector 32 to mate the insertion sheath 60 to the implantation device 24. In some embodiments, the control handle connector 32 of the handle 26 may mate with the hub 72 in only one orientation. In some embodiments, the hub 72 may include a major radial axis that is offset from the major radial axis of the handle 26. In some cases, the distal end 80 of the insertion sheath 60 may be beveled to accommodate the anchor 10 at the desired deployment angle for proper approximation to the wall 22 of the blood vessel 18. In some embodiments, the implantation device 24 can be inserted into the insertion sheath 60 at an orientation offset from the insertion sheath 60, but this is not required. It is contemplated that other suitable connectors may be used instead of the illustrative control handle connector 32 and hub 72, as desired.

Figure 2:
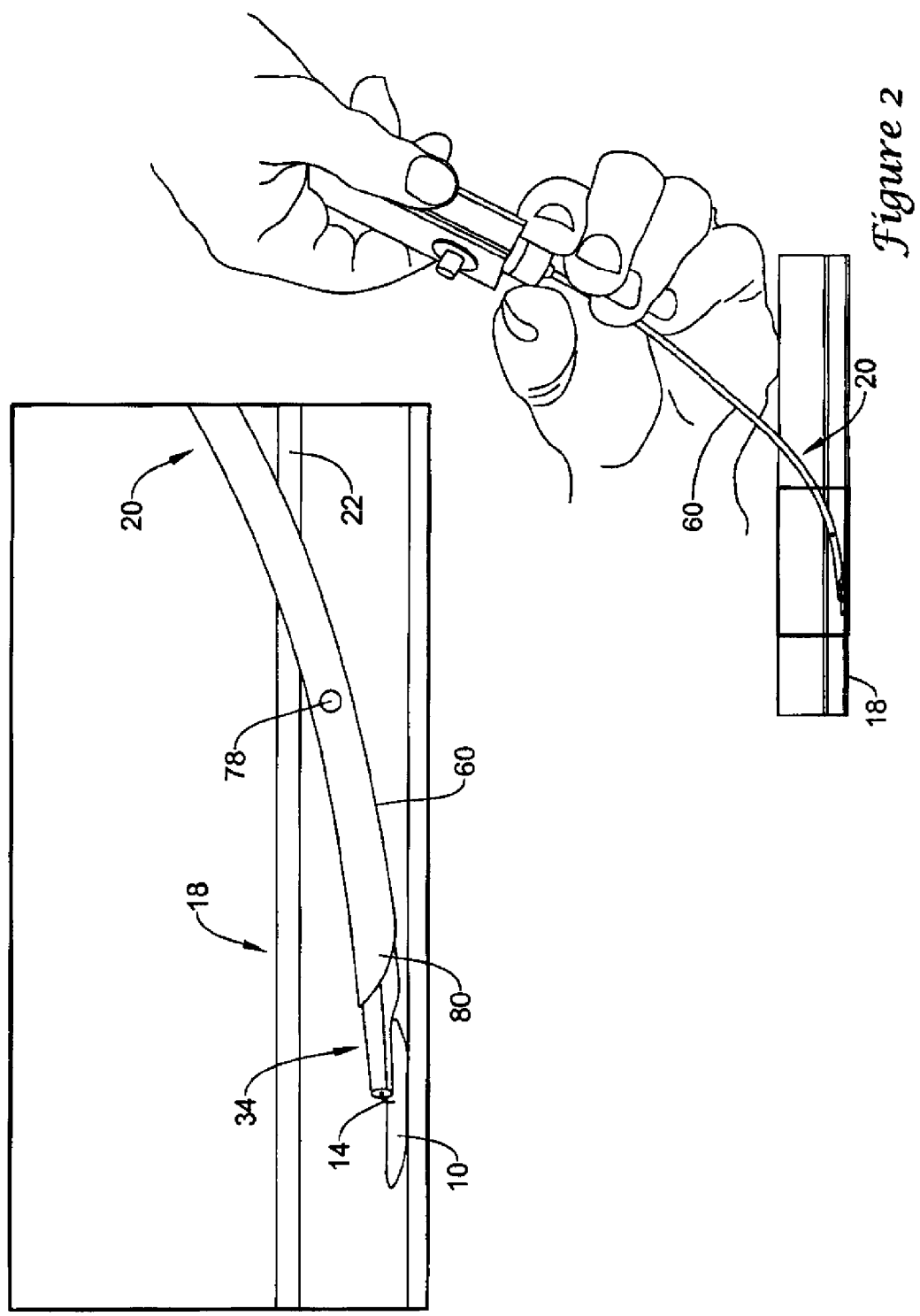
Figure 3:
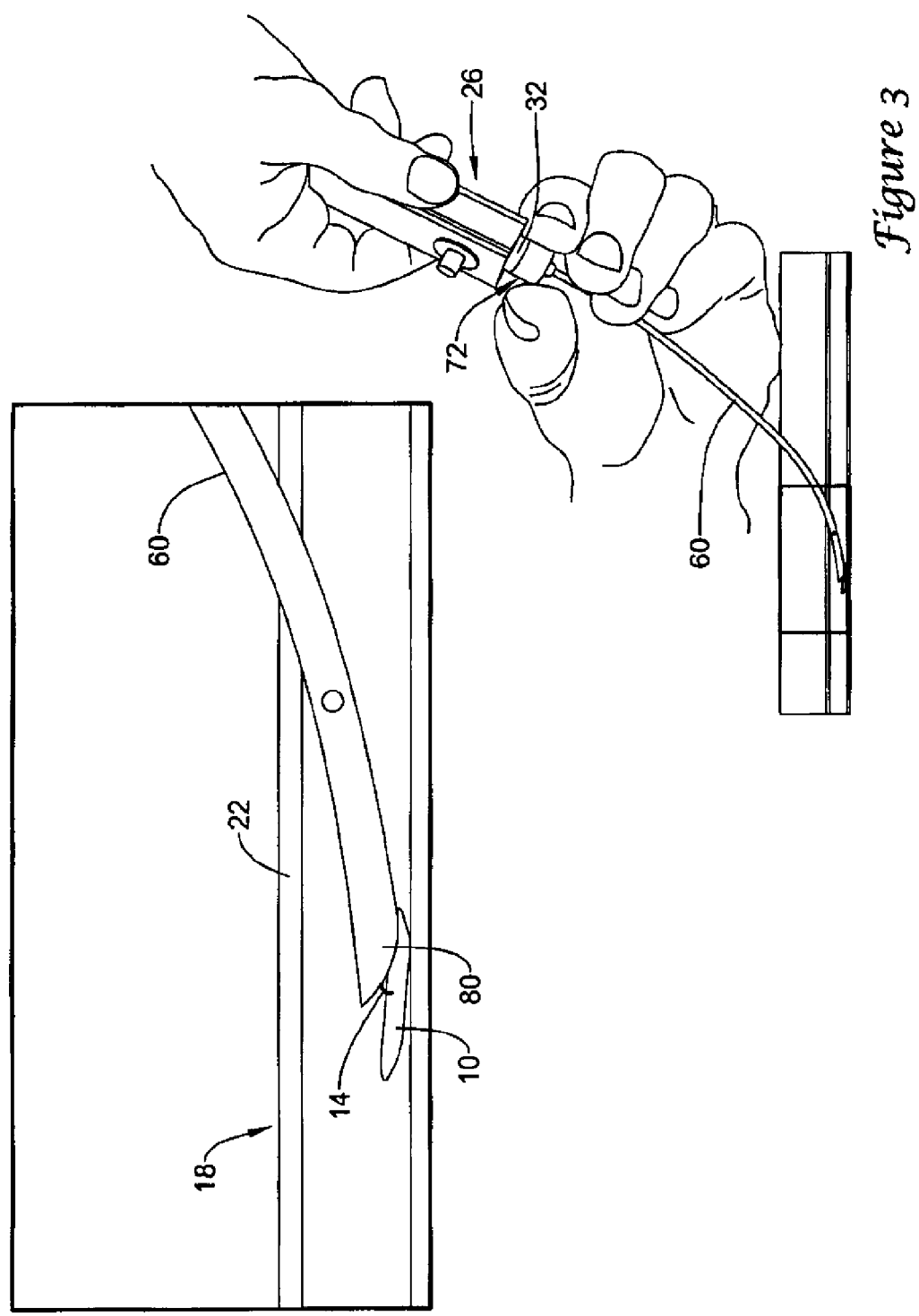
Figure 4:
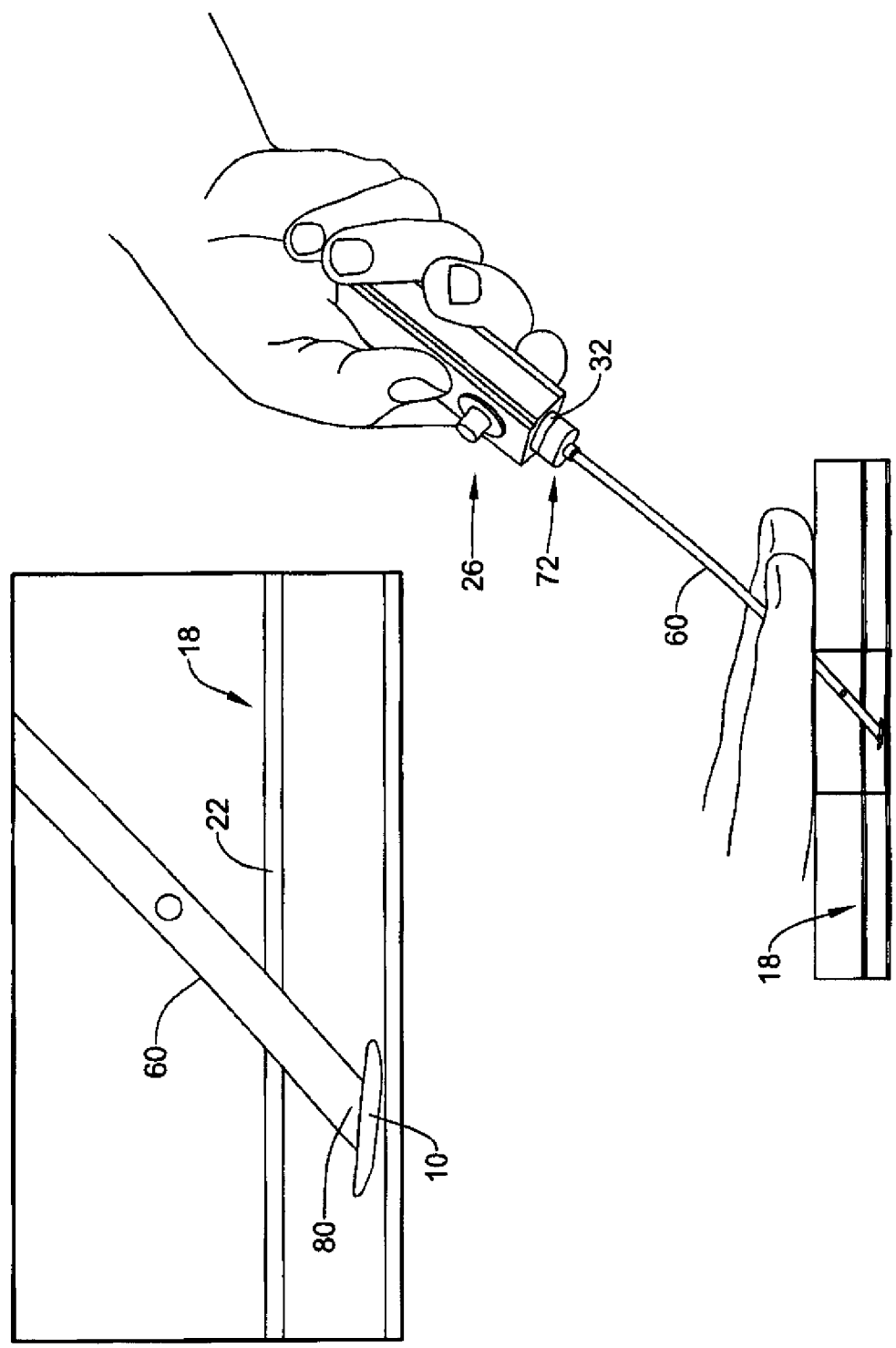
Figure 15:
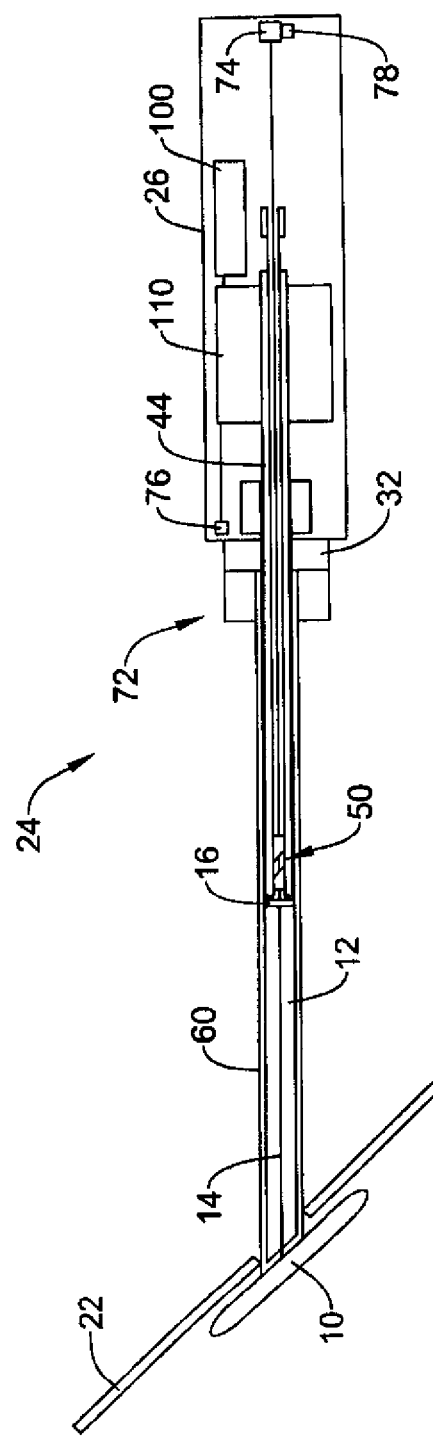

In some embodiments, the device sheath 34 of the implantation device 24 may be completely inserted into the insertion sheath 60. As shown in FIGS. 2 and 14, when the implantation device 24 is completely inserted, the anchor 10 is deployed out the distal end of the insertion sheath 60 into the blood vessel 18. When deployed, the anchor 10 may be initially spaced from the beveled distal end 80 of the insertion sheath 60, but, as shown in FIGS. 4 and 15, can be subsequently retracted, in some cases automatically, against the beveled distal end 80.

Figure 11:
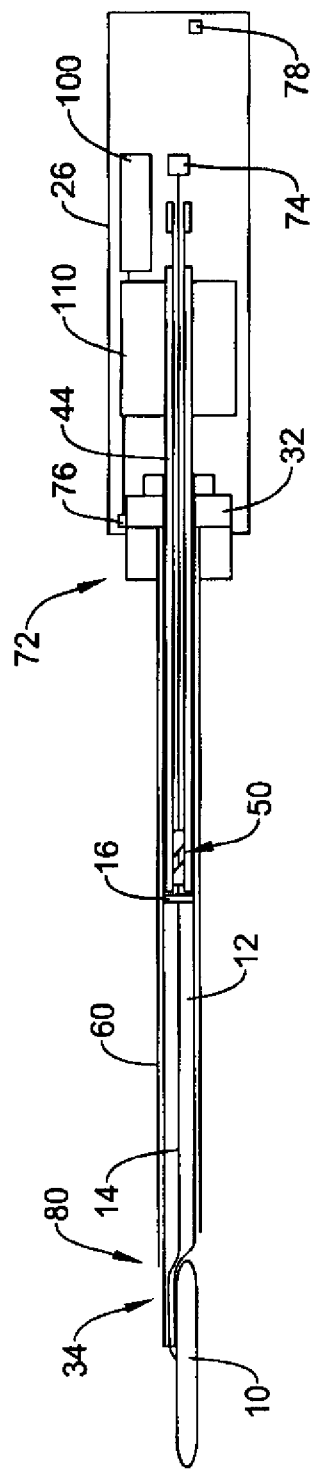
Figure 12:
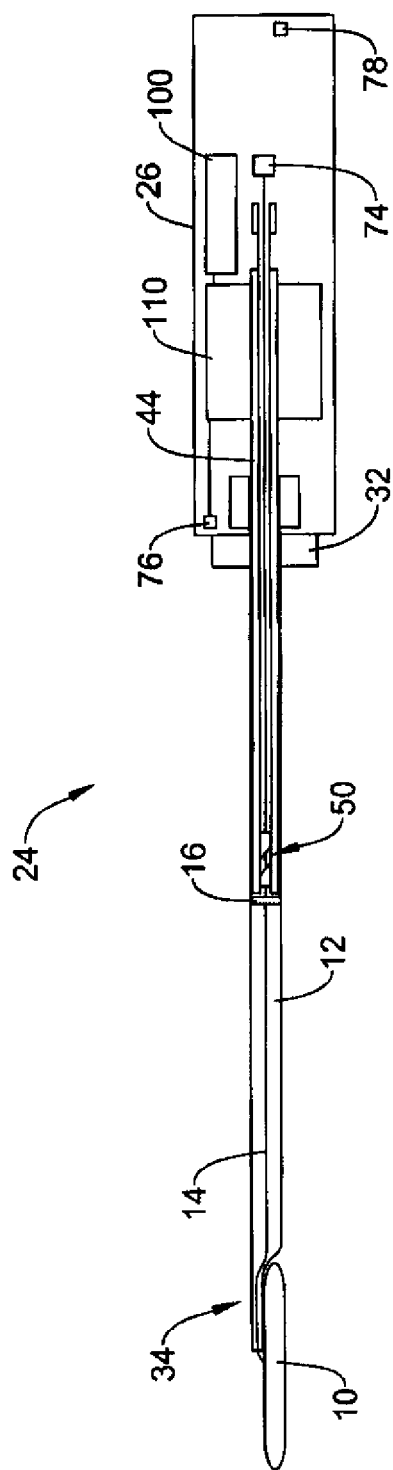

FIG. 11, for example, shows the implantation device 24 secured to the insertion sheath 60 before the anchor 10 has been seated. To do this, in some embodiments, the handle 26 of the implantation device 24 can be rotated relative to the insertion sheath 60 to align the hub 72 with the control handle connector 32. In some embodiments, the implantation device 24 can be rotated about 90 degrees when viewed from the proximal or distal end. The rotation may lock the control handle connector 32 to the hub 72 and actuate a seating mechanism 74. In some embodiments, the hub 72 may engage the control handle connector 32 to activate a position trigger 76. Position trigger 76 may be operatively connected to seating mechanism 74 such that activation of position trigger 76 may automatically actuate the seating mechanism 74. However, it is contemplated that other attachment, alignment, and/or release mechanisms may be used to connect the insertion sheath 60 to the implantation device 24 and to seat the anchor 10 against the distal end of the insertion sheath 60, as desired. Examples of such components that may be used can include interlocking snaps, torsion springs, spring releases, keys, push pins, and other suitable components, as desired.

In some embodiments, the seating mechanism 74 may translate the implantation device 24, including handle 26, anchor 10, suture 14, and device sheath 34, proximally relative to the insertion sheath 60 while the insertion sheath 60 is held in a fixed position. In some embodiments, the seating mechanism 74 may translate the insertion sheath 60 distally relative to the implantation device 24 while the implantation device 24 is held in a fixed position. In some embodiments a spring mechanism or motor may be the seating mechanism 74 that provides the translation discussed herein. In other embodiments, the seating mechanism 74 may be a spring mechanism or a motor configured to apply tension to the suture 14 by axially moving the proximal end of the suture 14 proximally within the handle 26. The relative movements described herein may translate the anchor 10 into contact with, or into close proximity to, the beveled distal end 80 of the insertion sheath 60. Alternatively, the seating mechanism 74 may include a combination of the above-described elements and/or motions which provide the relative movement required. The relative positioning of the anchor 10 and the distal end 80 after the anchor 10 has been seated as discussed herein may be seen, for example, in FIGS. 4 and 15.

Figure 5:
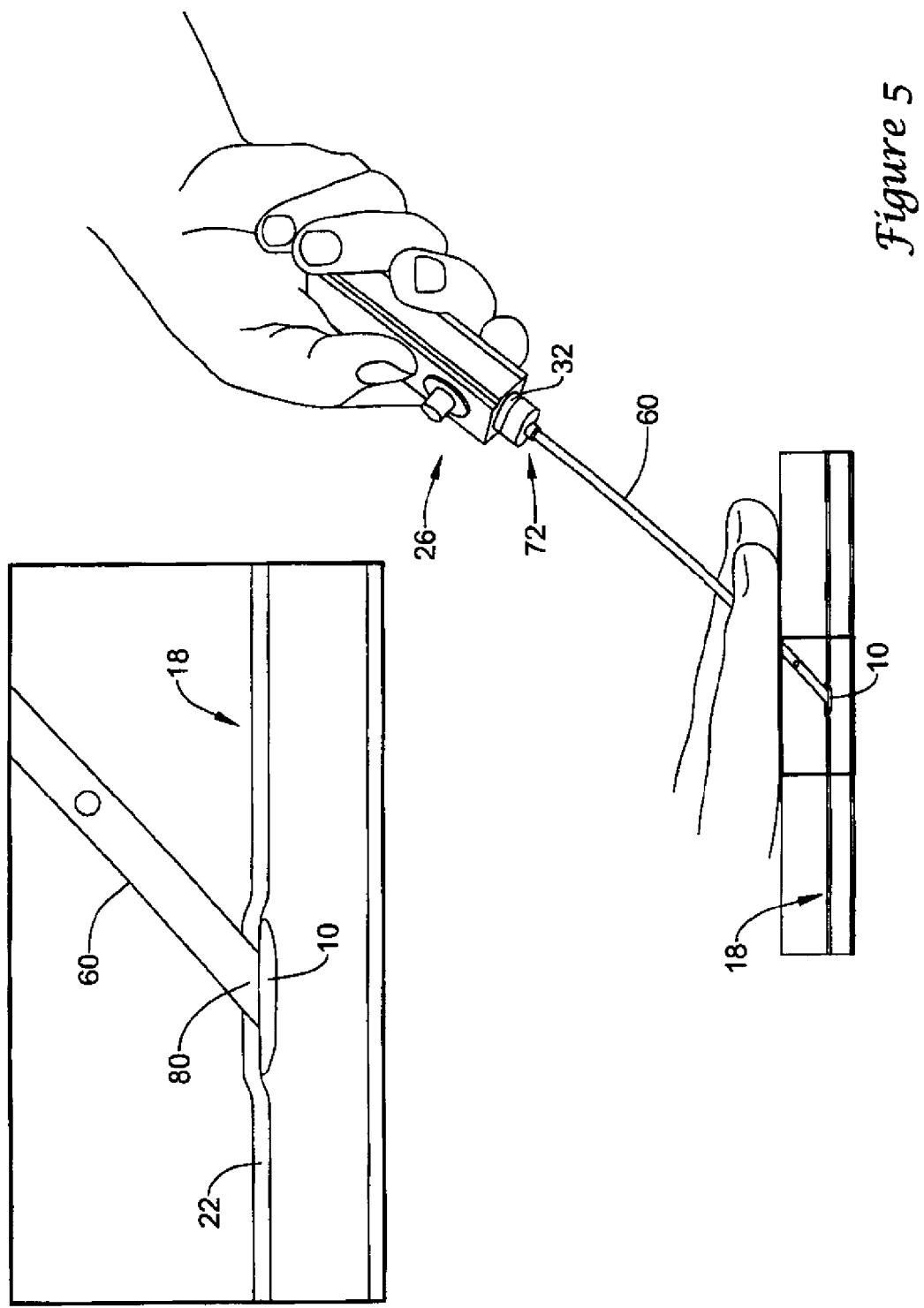

As shown in FIG. 5, the handle 26 and insertion sheath 60 can then be retracted or translated proximally to seat the anchor 10 against the interior surface of the vessel wall 22. With the anchor 10 seated against the interior surface of the vessel wall 22, tension may be continually applied to the handle 26 of implantation device 24.

Figure 6:
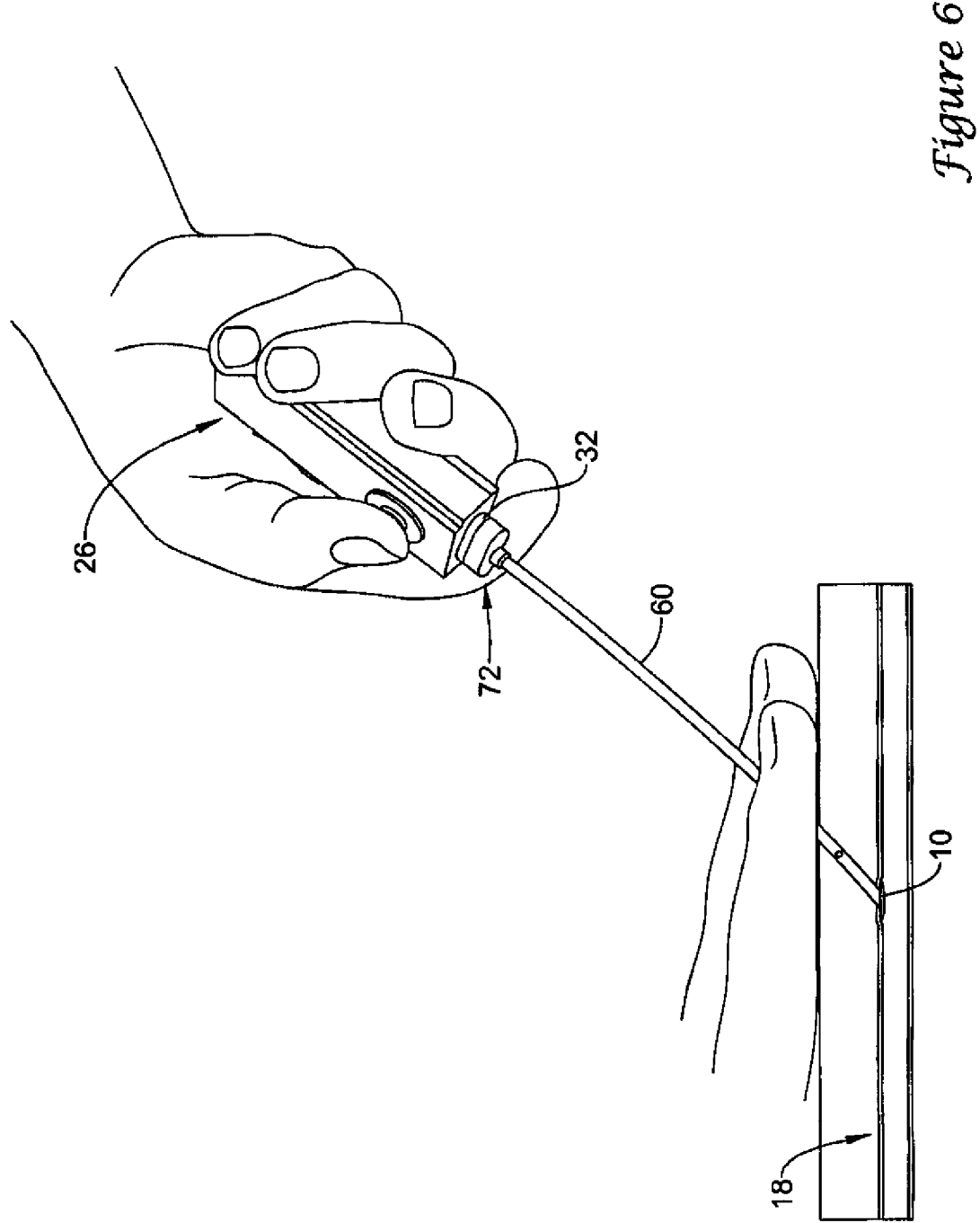

FIGS. 5 and 6 show the anchor 10 seated against the interior of the vessel wall 22 or arteriotomy. The suture 14 is coupled to the anchor 10 and extends proximally through the tissue tract 20. The plug 12 is disposed over the suture 14 adjacent the anchor 10 and the locking element 16 is disposed about the suture 14 proximal of the plug 12. The plug 12, suture 14, and locking element 16 may be disposed, at least partially, within the device sheath 34. At the step shown in FIG. 6, force trigger 78 may be activated automatically by tension on suture 14 as implantation device 24 is pulled proximally, or force trigger 78 may optionally be activated by the user pressing a manually-activated switch, as illustrated in FIG. 6.

As shown in FIGS. 7 and 16, the insertion sheath 60 may be retracted a distance from the anchor 10 and/or opening in the vessel wall 22 to provide a gap or an area for plug deployment. Insertion sheath 60, hub 72, and control handle connector 32 may be retracted proximally such that the hub 72 and the control handle connector 32 are at least partially withdrawn into the handle 26. Control handle connector 32 and the hub 72 may be completely withdrawn into the handle 26 in some embodiments. In one illustrative example, the distance may be about two-thirds of the length of the plug 12. For example, if the plug 12 is about three-quarters of an inch long in a non-axially compressed state, the distance that the insertion sheath 60 can be retracted may be about one-half inch. However, it is contemplated that others suitable distances may be used, as desired. As discussed above, the device sheath 34 and the handle 26 remain fixed in position relative to the anchor 10 and blood vessel 18.

Figure 8:
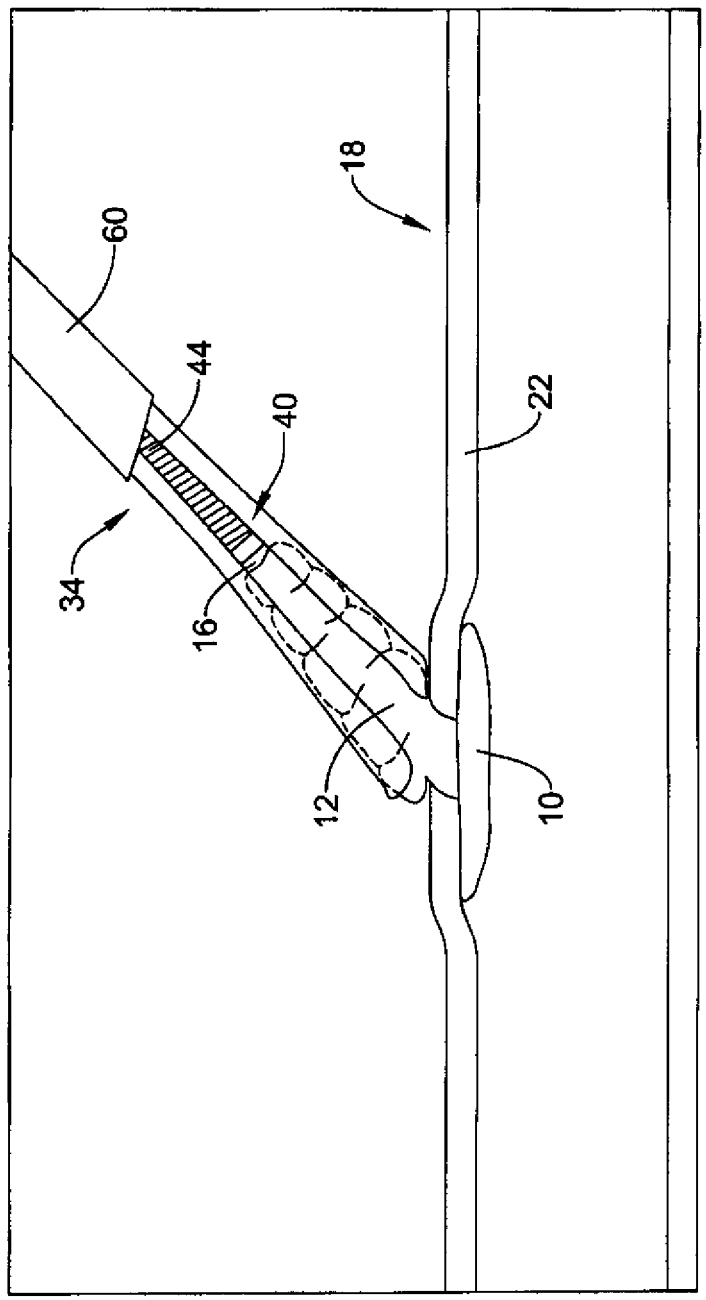
Figure 9:
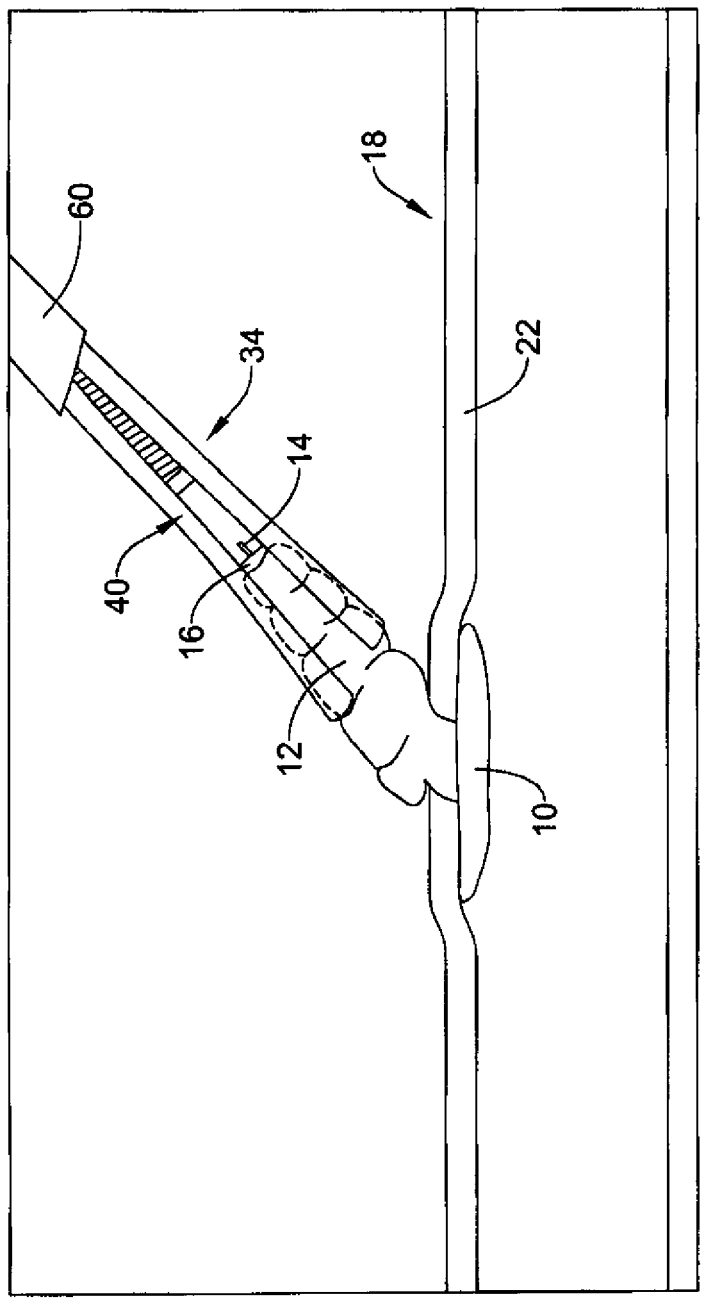
Figure 10:
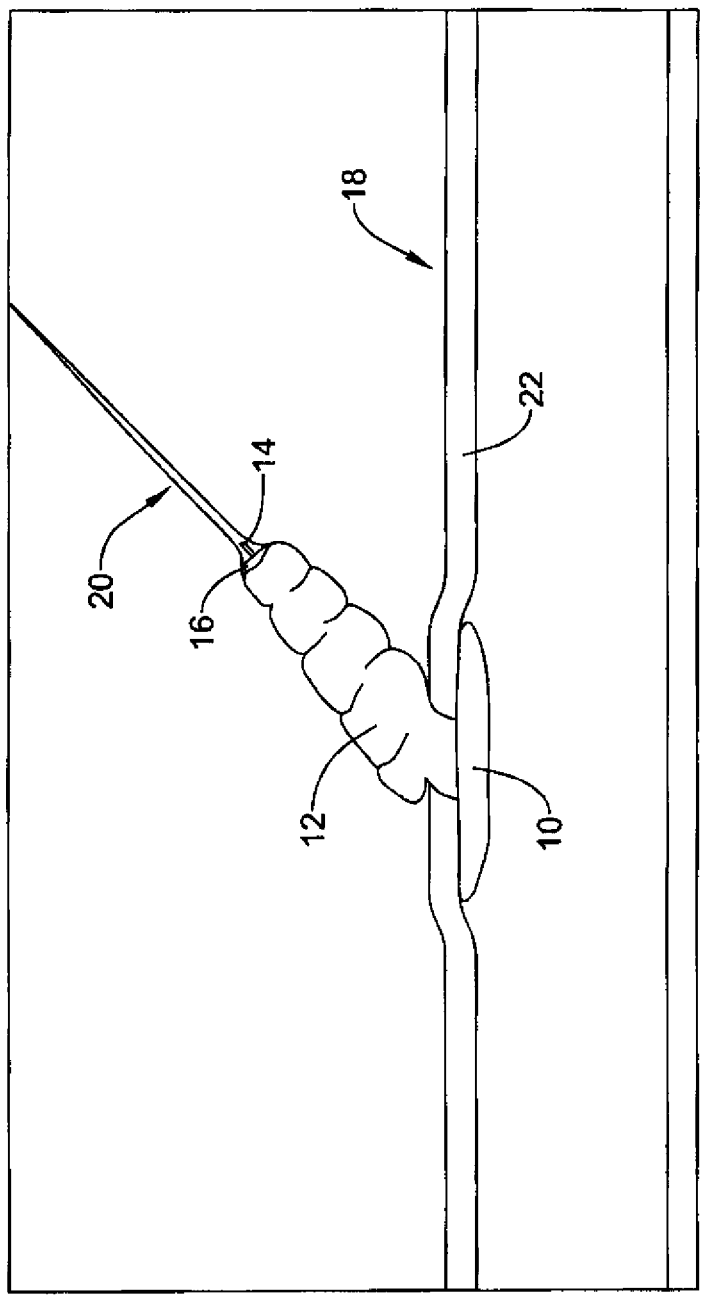

As shown in FIGS. 8 and 17, the plug 12 may be deployed in the tissue tract 20 while continuing to apply tension to the implantation device 24. The distal end of device sheath 34 may include at least one longitudinal slit 40. Deployment of the plug 12 may include axial compression and/or radial expansion. The at least one longitudinal slit 40 may widen as the plug 12 is axially compressed and/or radially expanded. The distal end of the device sheath 34 provides reduced friction for distal movement of the plug 12 during deployment compared to the plug 12 directly contacting tissue tract 20. This may result in reduced distal deployment force, improved plug cohesion, and/or reduced trauma to the tissue tract 20 and/or blood vessel 18.

With continued tension to the implantation device 24, an automatic suture release member 50 may be actuated to release the suture 14 from the implantation device 24. The automatic suture release member 50 may include other appropriate means of releasing the suture 14, such as, but not limited to, a collet that may release a proximal end of the suture 14, a loop disposed at a proximal end of the suture 14 which may be released from the handle 26, or a cutting element that may cut the suture 14. Suture 14 may be released or cut within or external to tissue tract 20, within or external to the insertion sheath 60, within or external to the device sheath 34, or a combination thereof. For example, suture 14 may be cut within the insertion sheath 60 while the insertion sheath 60 is disposed within the tissue tract 20.

As shown in FIGS. 9-10 and 18-19, the suture 14 is released from the implantation device 24 and then, the insertion sheath 60 and the implantation device 24 can be removed from the tissue tract 20 leaving the anchor 10, plug 12, suture 14, and locking element 16 to seal and/or close the opening in the vessel wall 22 and/or tissue tract 20. If the suture 14 extends proximally of the locking element 16 outside of the tissue tract 20, the extra length can be removed, such as, for example, by cutting. In other cases, the suture 14 may have a length such that no extra cutting may be needed. When the plug is exposed to a fluid, such as blood for example, the plug 12 can expand to fill the tissue tract 20 and/or opening in the vessel wall 22.

While the foregoing has described the implantation device 24 in detail, this is not meant to be limiting in any manner. It is contemplated that a suitable apparatus for sealing and/or closing an opening in a vessel wall and/or tissue tract can include other combinations of the above-described features.

Many of the steps described herein may occur automatically to streamline the procedure from a user perspective. For example, after inserting the device sheath 34 into the insertion sheath 60, the motor-driven deployment mechanism can be actuated to snug the anchor 10 against the end of the insertion sheath 60, translate the anchor 10 against the vessel wall 22, retract the insertion sheath 60 to provide clearance for deployment of the plug 12, compress and deploy the plug 12, cinch or lock the implant components to the vessel wall 22, and trim the suture 13 to length, all in sequence automatically.

Alternatively, various steps may be performed or actuated by the user when the user desires the particular steps to be performed. Various combinations of automatic, triggered, and manual steps can be utilized in different embodiments, with one or more motors providing plug compression and deployment or other required motions. For example, translating the anchor 10 against the vessel wall 22 may be done manually, while other steps are performed automatically.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method of deploying a vascular sealing plug in a patient, comprising:
   obtaining a vascular closure system, the vascular closure system comprising:
      an insertion sheath having a lumen therethrough;
      a device sheath adapted to be inserted into the lumen of the insertion sheath, the device sheath fixedly coupled to a handle extending therefrom, the handle adapted to be coupled to the insertion sheath;
      wherein the handle includes a stored energy source, a control system, and a motor each disposed therein; and
      a sealing assembly including an anchor disposed at a distal end of the device sheath and a suture operatively connecting the anchor to a vascular plug disposed within the distal end of the device sheath;
   inserting a distal end of the insertion sheath into a puncture through a wall of a blood vessel into a lumen of the blood vessel;
   inserting the device sheath into the insertion sheath with the anchor generally oriented axially to align with the device sheath;
   advancing the device sheath distally through the lumen of the insertion sheath until the anchor extends past the distal end of the insertion sheath;
   coupling the handle to the insertion sheath;
   after coupling the handle to the insertion sheath, actuating a seating mechanism to translate the anchor against the distal end of the insertion sheath and orient the anchor generally transverse to the insertion sheath;
   wherein coupling the handle to the insertion sheath activates a position trigger within the handle, wherein activating the position trigger automatically actuates the seating mechanism;
   withdrawing the insertion sheath and the handle proximally until the anchor is seated against an interior surface of the wall of the blood vessel;
   retracting the insertion sheath from the wall of the blood vessel while maintaining the device sheath and the handle in position for deployment of the vascular plug;
   actuating the motor, wherein the motor drives a push rod distally to deploy and axially compress the vascular plug at a controlled rate within the distal end of the device sheath;
   releasing the suture from the handle;
   withdrawing the handle, the device sheath, and the insertion sheath from the patient after releasing the suture.

2. The method of claim 1, wherein retracting the insertion sheath comprises activating a trigger operatively connected to the control system to actuate the motor, wherein the motor retracts the insertion sheath.

3. The method of claim 2, wherein the trigger is a manually-activated switch in communication with an exterior of the handle such that the switch may be actuated by an operator of the vascular closure system.

4. The method of claim 1, wherein releasing the suture from the handle includes cutting the suture.

5. The method of claim 1, wherein releasing the suture from the handle includes releasing an attachment element.

6. The method of claim 5, wherein the attachment element is a collet disposed about the suture, or the attachment element is a loop disposed at the proximal end of the suture.

7. The method of claim 1, wherein axially compressing the vascular plug results in radial expansion of the vascular plug.

8. The method of claim 7, wherein the distal end of the device sheath includes at least one longitudinal slit.

9. The method of claim 8, wherein the at least one longitudinal slit widens with the expansion of the vascular plug.

10. The method of claim 1, wherein inserting the device sheath into the insertion sheath with the anchor generally oriented axially to align with the device sheath deforms the distal end of the device sheath about the anchor.

11. A method of deploying a vascular sealing plug in a patient, comprising:
obtaining a vascular closure system, the vascular closure system comprising:
an insertion sheath having a lumen therethrough;
a device sheath adapted to be inserted into the lumen of the insertion sheath, the device sheath fixedly coupled to a handle extending therefrom, the handle adapted to be coupled to the insertion sheath;
wherein the handle includes a stored energy source, a control system, and a motor each disposed therein; and
a sealing assembly including an anchor disposed at a distal end of the device sheath and a suture operatively connecting the anchor to a vascular plug disposed within the distal end of the device sheath;
inserting a distal end of the insertion sheath into a puncture through a wall of a blood vessel into a lumen of the blood vessel;
inserting the device sheath into the insertion sheath with the anchor generally oriented axially to align with the device sheath;
advancing the device sheath distally through the lumen of the insertion sheath until the anchor extends past the distal end of the insertion sheath;
coupling the handle to the insertion sheath;
after coupling the handle to the insertion sheath, actuating a seating mechanism to translate the anchor against the distal end of the insertion sheath and orient the anchor generally transverse to the insertion sheath;
withdrawing the insertion sheath and the handle proximally until the anchor is seated against an interior surface of the wall of the blood vessel;
retracting the insertion sheath from the wall of the blood vessel while maintaining the device sheath and the handle in position for deployment of the vascular plug;
wherein retracting the insertion sheath comprises activating a trigger operatively connected to the control system to actuate the motor, wherein the motor retracts the insertion sheath;
wherein the trigger operatively connected to the control system is a force trigger responsive to tension applied to the suture as the anchor is seated against an interior surface of the wall of the blood vessel;
actuating the motor, wherein the motor drives a push rod distally to deploy and axially compress the vascular plug at a controlled rate within the distal end of the device sheath;
releasing the suture from the handle;
withdrawing the handle, the device sheath, and the insertion sheath from the patient after releasing the suture.

12. A vascular closure device, comprising:
a handle including a push rod extending distally therefrom, and a motor, a stored energy source, a control system, and a force trigger each disposed within the handle;
a device sheath having a proximal end, a distal end, and a first lumen extending therethrough, the proximal end fixedly coupled to an interior of the handle, wherein the push rod extends into the first lumen;
a vascular plug disposed within a distal end of the first lumen;
an intravascular anchor disposed at the distal end of the device sheath;
a suture operatively connected to the intravascular anchor and the handle, the suture extending proximally within the first lumen from the intravascular anchor through the vascular plug to the handle;
wherein the motor cooperates with the push rod to axially compress the vascular plug against the vessel wall in response to activation of the force trigger; and
an insertion sheath having a hub at a proximal end, a distal end, and a second lumen extending therethrough configured to accept the device sheath;
wherein the hub is configured to lockably engage the handle;
wherein lockably engaging the hub with the handle actuates a position trigger disposed within the handle, the position trigger thereby actuating a seating mechanism which translates the intravascular anchor against the distal end of the insertion sheath with the intravascular anchor oriented transversely to the insertion sheath.

13. The vascular closure device of claim 12, wherein the force trigger is activated by a predetermined amount of tension applied to the suture when the handle is moved proximally and the intravascular anchor is seated against the vessel wall.

14. The vascular closure device of claim 12, wherein the force trigger is activated by manually actuating a switch in communication with an exterior of the handle.

15. The vascular closure device of claim 12, further including a suture release member disposed within the device sheath, the suture release member configured to release the distal portion of the suture from the handle after the vascular plug has been axially compressed against the vessel wall.

16. The vascular closure device of claim 15, wherein the suture release member cuts the suture within the device sheath.

17. The vascular closure device of claim 12, wherein a proximal end of the suture is attached to the handle such that the proximal end of the suture cannot be moved outside of the handle.

* * * * *